(12) United States Patent
Sawyer et al.

(10) Patent No.: US 7,115,621 B2
(45) Date of Patent: Oct. 3, 2006

(54) CHEMICAL COMPOUNDS

(75) Inventors: Jason S. Sawyer, Indianapolis, IN (US); Mark W. Orme, Seattle, WA (US); James D. Copp, Greenwood, IN (US)

(73) Assignee: Lilly Icos LLC, Wilmington, DE (US)

( * ) Notice: Subject to any disclaimer, the term of this patent is extended or adjusted under 35 U.S.C. 154(b) by 75 days.

(21) Appl. No.: 10/471,476

(22) PCT Filed: Apr. 2, 2002

(86) PCT No.: PCT/US02/10367

§ 371 (c)(1),
(2), (4) Date: Feb. 9, 2004

(87) PCT Pub. No.: WO02/088123

PCT Pub. Date: Nov. 7, 2002

(65) Prior Publication Data

US 2004/0147542 A1    Jul. 29, 2004

Related U.S. Application Data

(60) Provisional application No. 60/286,730, filed on Apr. 25, 2001.

(51) Int. Cl.
A61K 31/44    (2006.01)

(52) U.S. Cl. .............. 514/292; 514/126; 514/253.03; 546/84; 546/87; 544/232.8; 544/361

(58) Field of Classification Search .............. 546/84, 546/87; 544/232.8, 361; 514/292, 126, 514/253.03
See application file for complete search history.

(56) References Cited

U.S. PATENT DOCUMENTS

| | | | | |
|---|---|---|---|---|
| 4,336,260 A | * | 6/1982 | Payne et al. | 514/292 |
| 5,859,006 A | * | 1/1999 | Daugan | 514/249 |
| 6,043,252 A | * | 3/2000 | Bombrun | 514/292 |
| 6,069,150 A | | 5/2000 | Spinelli et al. | |
| 6,117,881 A | * | 9/2000 | Bombrun | 514/292 |
| 6,306,870 B1 | * | 10/2001 | Bombrun | 514/292 |
| 6,492,358 B1 | * | 12/2002 | Sui et al. | 514/232.8 |
| 2003/0225092 A1 | * | 12/2003 | Orme et al. | 514/249 |

FOREIGN PATENT DOCUMENTS

| | | | |
|---|---|---|---|
| BE | 612725 | * | 7/1962 |
| EP | 0 466 548 | | 1/1992 |
| JP | 49048700 | * | 5/1974 |
| JP | 49048700 A2 | * | 5/1974 |
| JP | 59036676 A2 | * | 2/1984 |
| WO | WO 96/32003 | | 10/1996 |
| WO | WO 97/37658 | * | 10/1997 |
| WO | WO 97/43267 | | 11/1997 |
| WO | WO 00/15639 | | 3/2000 |
| WO | WO 01/08686 | | 2/2001 |
| WO | WO 01/87038 | | 11/2001 |
| WO | WO 01/94347 | | 12/2001 |
| WO | WO 02/28865 | | 4/2002 |
| WO | WO 02/36593 | | 5/2002 |

OTHER PUBLICATIONS

Srivastava et al. Bioorganic & Medicinal Chemistry. (1999) 7:1223-1236.*
Akimoto et al. Chemical & Pharmaceutical Bulletin (1974), 22(11): 2614-23.*
Bojarski et al. Pharmazie (1993), 48(4): 289-94.*
Fantauzzi et al. Tetrahedron Letters (1998), 39(11): 1291-1294.*
Saxena et al. Indian Journal of Chemistry (1973), 11(5): 417-21.*
Ukita et. al. J. Med. Chem. 2001. 44:2204-2218.*
Rotella D. Nature Reviews/Drug Discovery. 2002. 1:674-682.*
S. Kumar et al., *Indian Journal of Chemistry*, vol. 22B, pp. 54-59 (1983).
S.K. Srivastava et al., *Bioorganic & Medicinal Chemistry*, 7, 1223-1236 (1999).
A. Ishida et al., *Chem. Pharm. Bull.*, 33(8), 3237-3249 (1985).

* cited by examiner

*Primary Examiner*—Amelia A. Owens
*Assistant Examiner*—Evelyn Huang
(74) *Attorney, Agent, or Firm*—Marshall, Gerstein & Borun LLP

(57) ABSTRACT

Compounds of general structural formula (I) and use of the compounds and salts and solvates thereof, as therapeutic agents as inhibitors of phosphodiesterase 5 cardiovascular disorders (I)

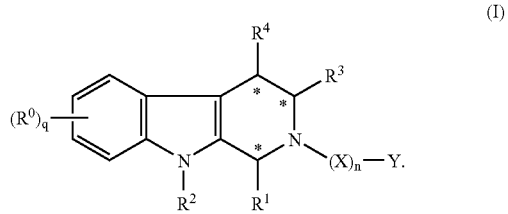

39 Claims, No Drawings

CHEMICAL COMPOUNDS

CROSS-REFERENCE TO RELATED APPLICATIONS

This is the U.S. national phase application of International Application No. PCT/US02/10367, filed Apr. 2, 2002, which claims the benefit of U.S. provisional patent application Ser. No. 60/286,730, filed Apr. 25, 2001.

FIELD AND BACKGROUND OF THE INVENTION

This invention relates to a series of compounds, to methods of preparing the compounds, to pharmaceutical compositions containing the compounds, and to their use as therapeutic agents. In particular, the invention relates to compounds that are potent and selective inhibitors of cyclic guanosine 3',5'-monophosphate specific phosphodiesterase (cGMP-specific PDE), in particular PDE5, and have utility in a variety of therapeutic areas wherein such inhibition is considered beneficial, including the treatment of cardiovascular disorders and erectile dysfunction.

SUMMARY OF THE INVENTION

The present invention provides compounds of formula (I)

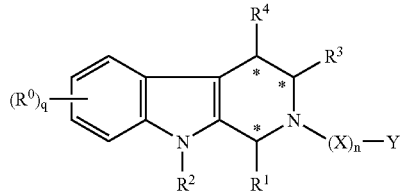

wherein $R^0$, independently, is selected from the group consisting of halo, $C_{1-6}$alkyl, aryl, heteroaryl, $C_{3-8}$cycloalkyl, $C_{3-8}$heterocycloalkyl, $C_{3-8}$cycloalkylQ, $C(=O)R^a$, $OC(=O)R^a$, $C(=O)OR^a$, $C_{1-4}$alkyleneNR$^a$R$^b$, $C_{1-4}$alkyleneHet, $C_{1-4}$alkyleneC(=O)OR$^a$, $C(=O)NR^aSO_2R^c$, $C(=O)C_{1-4}$alkyleneHet, $C(=O)NR^aR^b$, $C(=O)NR^aR^c$, $C(=O)NR^aC_{1-4}$alkyleneOR$^b$, $C(=O)NR^aC_{1-4}$alkyleneHet, $OR^a$, $OC_{1-4}$alkyleneC(=O)OR$^a$, $OC_{1-4}$alkyleneNR$^a$R$^b$, $OC_{1-4}$alkyleneHet, $OC_{1-4}$alkyleneOR$^a$, $OC_{1-4}$alkyleneNR$^a$C(=O)OR$^b$, $NR^aR^b$, $NR^aC_{1-4}$alkyleneNR$^a$R$^b$, $NR^aC(=O)R^b$, $NR^aC(=O)NR^aR^b$, $N(SO_2C_{1-4}$alkyl$)_2$, $NR^a(SO_2C_{1-4}$alkyl$)$, nitro, trifluoromethyl, trifluoromethoxy, cyano, $SO_2NR^aR^b$, $SO_2R^a$, $SOR^a$, $SR^a$, and $OSO_2CF_3$;

$R^1$ is selected from the group consisting of optionally substituted aryl, optionally substituted heteroaryl, an optionally substituted $C_{3-8}$cycloalkyl ring, an optionally substituted $C_{3-8}$heterocycloalkyl ring, an optionally substituted bicyclic ring

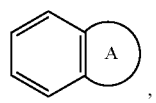

wherein the fused ring A is a 5- or 6-membered ring, saturated or partially or fully unsaturated, and comprises carbon atoms and optionally one to three heteroatoms selected from oxygen, sulfur, and nitrogen, hydrogen, $C_{1-6}$alkyl, aryl$C_{1-3}$alkyl, $C_{1-3}$alkylenearyl, halo$C_{1-6}$alkyl, $C_{1-4}$alkyleneC(=O)OR$^a$, $C_{1-4}$alkyleneC(=O)NR$^a$R$^b$, $C_{3-8}$cycloalkyl, $C_{3-8}$cycloalkenyl, $C_{3-8}$heterocycloalkenyl, $C_{1-4}$alkyleneHet, $C_{1-4}$alkylene-QR$^a$, $C_{2-6}$alkenyleneQR$^a$, $C_{1-4}$alkyleneQC$_{1-4}$alkyleneQR$^a$,

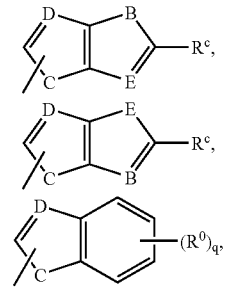

and a spiro substituent having a structure

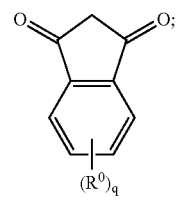

$R^2$ is selected from the group consisting of hydrogen, $C_{1-6}$alkyl, $C_{3-8}$cycloalkyl, $C_{3-8}$heterocycloalkyl, $C_{2-6}$alkenyl, $C_{1-3}$alkylenearyl, aryl$C_{1-3}$alkyl, $C(=O)R^a$, aryl, heteroaryl, $C(=O)R^a$, $C(=O)NR^aR^b$, $C(=O)NR^aR^c$, $C(=S)NR^aR^b$, $C(=S)NR^aR^c$, $SO_2R^a$, $SO_2NR^aR^b$, $S(=)R^a$, $S(=O)NR^aR^b$, $C(=O)NR^aC_{1-4}$alkyleneOR$^a$, $C(=O)NR^aC_{1-4}$alkyleneHet, $C(=O)C_{1-4}$alkylenearyl, $C(=O)C_{1-4}$alkyleneheteroaryl, $C_{1-4}$alkylenearyl substituted with one or more of $SO_2NR^aR^b$, $NR^aR^b$, $C(=O)OR^a$, $NR^aSO_2CF_3$, $CN$, $NO_2$, $C(=O)R^a$, $OR^a$, $C_{1-4}$alkyleneNR$^a$R$^b$, and $OC_{1-4}$alkyleneNR$^a$R$^b$, $C_{1-4}$alkyleneheteroaryl, $C_{1-4}$alkyleneHet, $C_{1-4}$alkyleneC(=O)C$_{1-4}$alkylenearyl, $C_{1-4}$alkyleneC(=O)C$_{1-4}$alkylene-heteroaryl, $C_{1-4}$alkyleneC(=O)Het, $C_{1-4}$alkyleneC(=O)NR$^a$R$^b$, $C_{1-4}$alkyleneOR$^a$, $C_{1-4}$alkyleneNR$^a$C(=O)R$^a$, $C_{1-4}$alkyleneOC$_{1-4}$alkyleneOR$^a$, $C_{1-4}$alkyleneNR$^a$R$^b$, $C_{1-4}$alkyleneC(=O)OR$^a$, and $C_{1-4}$alkyleneOC$_{1-4}$alkyleneC(=O)OR$^a$;

$R^3$ is selected from the group consisting of $C(=O)R^b$, $C(=O)OR^b$, $C(=O)NR^aR^b$, $C(=O)NR^aR^c$, $C(=S)NR^aR^b$, $C(=S)NR^aR^c$, $C(=O)Het$, $C(=O)NR^aC_{1-4}$alkyleneOR$^a$, $C(=O)NR^aC_{1-4}$alkyleneHet, $C(=O)C_{1-4}$alkylenearyl, $C(=O)C_{1-4}$alkyleneheteroaryl, $C(=O)NR^aC_{1-4}$alkylenearyl, $C(=O)NR^aC_{1-4}$alkyleneC$_{3-8}$cycloalkyl, $C(=O)NR^bSO_2R^c$, $C(=O)NR^aC_{1-4}$alkyleneOC$_{1-6}$alkyl, $C(=O)NR^aC_{1-4}$alkyleneheteroaryl, $NR^aR^c$, $NR^aC(=O)R^b$, $NR^aC(=O)NR^aR^c$, $NR^a(SO_2C_{1-4}$alkyl), $N(SO_2C_{1-4}$alkyl$)_2O$, $R^a$, $NR^aC(=O)C_{1-4}$alkyleneN(R$^b$)$_2$, $NR^aC(=O)C_{1-4}$alkyleneC(=O)OR$^a$, $NR^a(C=O)C_{1-3}$alkylenearyl, $NR^aC(=O)C_{1-3}$alkylene-$C_{3-8}$heterocycloalkyl, $NR^aC(=O)C_{1-3}$alkyleneHet, and $C(=O)NR^aSO_2R^b$;

$R^4$ is selected from the group consisting of hydrogen, $C_{1-6}$alkyl, aryl, heteroaryl, aryl$C_{1-3}$alkyl, $C_{1-3}$alkylenearyl, $C_{1-3}$alkyleneHet, $C_{3-8}$cycloalkyl, and $C_{3-8}$heterocycloalkyl;

X is selected from the group consisting of C(=O), $(CH_2)_tC(=O)$, C(=O)C≡C, $C(=O)C(R^a)=C(R^a)$, C(=S), SO, $SO_2$, $SO_2C(R^a)=CR^a$, $CR^aR^b$, $CR^a=CR^a$, C(=O)$NR^a$, and C(=N—$OR^a$);

Y is selected from the group consisting of $R^a$, $R^d$, $(CH_2)_n$ C(=O)$R^c$, $N(R^b)(CH_2)_nR^c$, $O(CH_2)_nR^c$, $N(R^b)C(=O)R^c$, C(=O)N($R^a$)($R^c$), $N(R^a)C(=O)R^c$,

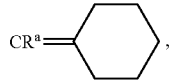

and $N(R^a)SO_2R^c$;

$R^a$ is selected from the group consisting of hydrogen, $C_{1-6}$alkyl, $C_{3-6}$cycloalkyl, aryl, aryl$C_{1-3}$alkyl, $C_{1-3}$alkylenearyl, heteroaryl, heteroaryl$C_{1-3}$alkyl, and $C_{1-3}$alkyleneheteroaryl;

$R^b$ is selected from the group consisting of hydrogen, $C_{1-6}$alkyl, $C_{3-8}$cycloalkyl, $C_{1-3}$alkyleneN($R^a$)$_2$, aryl, aryl$C_{1-3}$ alkyl, $C_{1-3}$alkylenearyl, and heteroaryl;

$R^c$ is selected from the group consisting of hydrogen, $C_{1-6}$alkyl, aryl, heteroaryl, aryl$C_{1-3}$alkyl, heteroaryl$C_{1-3}$alkyl, $C_{1-3}$alkyleneN($R^a$)$_2$, $C_{1-6}$alkylenearyl, $C_{1-6}$alkyleneHet, halo$C_{1-6}$alkyl, $C_{3-8}$cycloalkyl, $C_{3-8}$heterocycloalkyl, Het, $C_{1-3}$alkyleneheteroaryl, $C_{1-6}$alkyleneC(=O)$OR^a$, and $C_{1-3}$alkylene$C_{3-8}$heterocycloalkyl;

or $R^a$ and $R^c$ are taken together to form a 5- or 6-membered ring, optionally containing at least one heteroatom;

$R^d$ is a 5- or 6-membered ring or a bicyclic fused ring system, saturated or partially or fully unsaturated, comprising carbon atoms and optionally one to three heteroatoms selected from oxygen, sulfur, and nitrogen, and optionally substituted with one or more $R^e$ or $R^f$;

$R^e$ is selected from the group consisting of
nitro,
trifluoromethyl,
trifluoromethoxy,
halogen,
cyano,
Het,
$C_{1-6}$alkyl,
$C_{1-6}$alkyleneOR$^a$,
C(=O)$R^a$,
OC(=O)$R^a$,
C(=O)$OR^a$,
$C_{1-4}$alkyleneHet,
$C_{1-4}$alkyleneC(=O)$OR^a$,
O$C_{1-4}$alkyleneC(=O)$OR^a$,
$C_{1-4}$alkyleneO$C_{1-4}$alkyleneC(=O)$OR^a$,
C(=O)NR$^a$SO$_2$R$^f$,
C(=O)$C_{1-4}$alkyleneHet,
$C_{1-4}$alkyleneNR$^a$R$^b$,
$C_{2-6}$alkenyleneNR$^a$R$^b$,
C(=O)NR$^a$R$^b$,
C(=O)NR$^a$R$^b$,
C(=O)NR$^a$$C_{1-4}$alkyleneOR$^b$,
C(=O)NR$^a$$C_{1-4}$alkyleneHet,
OR$^a$,
O$C_{2-4}$alkyleneNR$^a$R$^b$,
O$C_{1-4}$alkyleneCH(OR$^a$)CH$_2$—NR$^a$R$^b$,
O$C_{1-4}$alkyleneHet,
O$C_{2-4}$alkyleneOR$^a$,
O$C_{2-4}$alkyleneNR$^a$C(=O)OR$^b$,
NR$^a$R$^b$,
NR$^a$$C_{1-4}$alkyleneNR$^a$R$^b$,
NR$^a$C(=O)R$^b$,
NR$^a$C(=O)NR$^a$R$^b$,
N(SO$_2$$C_{1-4}$alkyl)$_2$,
NR$^a$(SO$_2$$C_{1-4}$alkyl),
SO$_2$NR$^a$R$^b$,
and OSO$_2$trifluoromethyl;

$R^f$ is selected from the group consisting of hydrogen, halogen, OR$^a$, $C_{1-6}$alkyl, nitro, and NR$^a$R$^b$;

or $R^e$ and $R^f$ are taken together to form a 3- or 4-membered alkylene or alkenylene chain component of a 5- or 6-membered ring, optionally containing at least one heteroatom;

$R^g$ is phenyl or $C_{4-6}$cycloalkyl, optionally substituted with one or more halogen, C(=O)OR$^a$, or OR$^a$;

Q is O, S, or NR$^h$;
B is O, S, or NR$^h$;
C is O, S, or NR$^a$;
D is CR$^a$ or N;
E is CR$^a$, C(R$^a$)$_2$, or NR$^h$; and $R^h$ is null or is selected from the group consisting of hydrogen, $C_{1-6}$alkyl, aryl, heteroaryl, aryl$C_{1-3}$alkyl, heteroaryl$C_{1-3}$alkyl, $C_{1-3}$alkylenearyl, and $C_{1-3}$alkyleneheteroaryl;

Het represents a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)OR$^a$;

n is 0 or 1;
q is 0, 1, 2, 3, or 4;
t is 1, 2, 3, or 4;

and pharmaceutically acceptable salts and solvates (e.g., hydrates) thereof.

The present invention also provides compounds of structural formula (Ia), i.e., compounds of structural formula (I) wherein (X)$_n$—Y is hydrogen, i.e., a compound having a formula

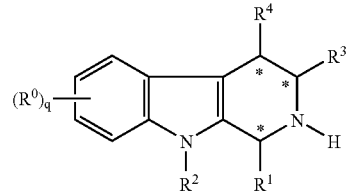

wherein $R^0$, independently, is selected from the group consisting of halo, $C_{1-6}$alkyl, aryl, heteroaryl, $C_{3-8}$cycloalkyl, $C_{3-8}$heterocycloalkyl, $C_{3-8}$cycloalkylQ, C(=O)R$^a$, OC(=O)R$^a$, C(=O)OR$^a$, $C_{1-4}$alkyleneNR$^a$R$^b$, $C_{1-4}$alkyleneHet, $C_{1-4}$alkyleneC(=O)OR$^a$, C(=O)NR$^a$SO$_2$R$^c$, C(=O)$C_{1-4}$alkyleneHet, C(=O)NR$^a$R$^b$, C(=O)NR$^a$R$^c$, C(=O)NR$^a$$C_{1-4}$alkyleneOR$^b$, C(=O)NR$^a$$C_{1-4}$alkyleneHet, OR$^a$, O$C_{1-4}$alkyleneC(=O)OR$^a$, O$C_{1-4}$alkyleneNR$^a$R$^b$, O$C_{1-4}$alkyleneHet, O$C_{1-4}$alkyleneOR$^a$, O$C_{1-4}$alkyleneNR$^a$C(=O)OR$^b$, NR$^a$R$^b$, NR$^a$$C_{1-4}$alkyleneNR$^a$R$^b$, NR$^a$C(=O)R$^b$, NR$^a$C(=O)NR$^a$R$^b$, N(SO$_2$$C_{1-4}$alkyl)$_2$, NR$^a$(SO$_2$$C_{1-4}$alkyl), nitro, trifluoromethyl, trifluoromethoxy, cyano, SO$_2$NR$^a$R$^b$, SO$_2$R$^a$, SOR$^a$, SR$^a$, and OSO$_2$CF$_3$;

$R^1$ is selected from the group consisting of optionally substituted aryl, optionally substituted heteroaryl, an optionally substituted $C_{3-8}$cycloalkyl ring, an optionally substituted $C_{3-8}$heterocycloalkyl ring, an optionally substituted bicyclic ring

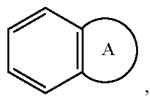

wherein the fused ring A is a 5- or 6-membered ring, saturated or partially or fully unsaturated, and comprises carbon atoms and optionally one to three heteroatoms selected from oxygen, sulfur, and nitrogen, hydrogen, $C_{1-6}$alkyl, aryl$C_{1-3}$alkyl, $C_{1-3}$alkylenearyl, halo$C_{1-6}$alkyl, $C_{1-4}$alkyleneC(=O)OR$^a$, $C_{1-4}$alkyleneC(=O)NR$^a$R$^b$, $C_{3-8}$cycloalkyl, $C_{3-8}$cycloalkenyl, $C_{3-8}$heterocycloalkenyl, $C_{1-4}$alkyleneHet, $C_{1-4}$alkyleneQR$^a$, $C_{2-6}$alkenyleneQR$^a$, $C_{1-4}$alkyleneQC$_{1-4}$alkyleneQR$^a$,

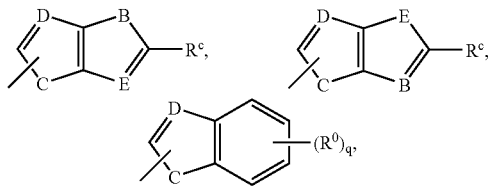

and a spiro substituent having a structure

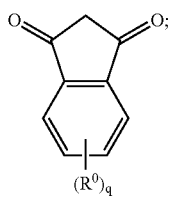

$R^2$ is selected from the group consisting of hydrogen, $C_{1-6}$alkyl, $C_{3-8}$cycloalkyl, $C_{3-8}$heterocycloalkyl, $C_{2-6}$alkenyl, $C_{1-3}$alkylenearyl, aryl$C_{1-3}$alkyl, C(=O)R$^a$, aryl, heteroaryl, C(=O)R$^a$, C(=O)NR$^a$R$^b$, C(=O)NR$^a$R$^c$, C(=S)NR$^a$R$^b$, C(=S)NR$^a$R$^c$, SO$_2$R$^a$, SO$_2$NR$^a$R$^b$, S(=O)R$^a$, S(=O)NR$^a$R$^b$, C(=O)NR$^a$C$_{1-4}$alkyleneOR$^a$, C(=O)NR$^a$C$_{1-4}$alkyleneHet, C(=O)C$_{1-4}$alkylenearyl, C(=O)C$_{1-4}$alkyleneheteroaryl, C$_{1-4}$alkylenearyl substituted with one or more of SO$_2$NR$^a$R$^b$, NR$^a$R$^b$, C(=O)OR$^a$, NR$^a$SO$_2$CF$_3$, CN, NO$_2$, C(=O)R$^a$, OR$^a$, C$_{1-4}$alkyleneNR$^a$R$^b$, and OC$_{1-4}$alkyleneNR$^a$R$^b$, C$_{1-4}$alkyleneheteroaryl, C$_{1-4}$alkyleneHet, C$_{1-4}$alkyleneC(=O)C$_{1-4}$alkylenearyl, C$_{1-4}$alkyleneC(=O)C$_{1-4}$alkyleneheteroaryl, C$_{1-4}$alkyleneC(=O)Het, C$_{1-4}$alkyleneC(=O)NR$^a$R$^b$, C$_{1-4}$alkyleneOR$^a$, C$_{1-4}$alkyleneNR$^a$C(=O)R$^a$, C$_{1-4}$alkyleneOC$_{1-4}$alkyleneOR$^a$, C$_{1-4}$alkyleneNR$^a$R$^b$, C$_{1-4}$alkyleneC(=O)OR$^a$, and C$_{1-4}$alkyleneOC$_{1-4}$alkyleneC(=O)OR$^a$;

$R^3$ is selected from the group consisting of C(=O)R$^b$, C(=O)OR$^b$, C(=O)NR$^a$R$^b$, C(=O)NR$^a$R$^c$, C(=S)NR$^a$R$^b$, C(=S)NR$^a$R$^c$, C(=O)Het, C(=O)NR$^a$C$_{1-4}$alkyleneOR$^a$, C(=O)NR$^a$C$_{1-4}$alkyleneHet, C(=O)C$_{1-4}$alkylenearyl, C(=O)C$_{1-4}$alkyleneheteroaryl, C(=O)NR$^a$C$_{1-4}$alkylenearyl, C(=O)NR$^a$C$_{1-4}$alkyleneC$_{3-8}$cycloalkyl, C(=O)NR$^b$SO$_2$R$^c$, C(=O)NR$^a$C$_{1-4}$alkyleneOC$_{1-6}$alkyl, C(=O)NR$^a$C$_{1-4}$alkyleneheteroaryl, NR$^a$R$^c$, NR$^a$C(=O)R$^b$, NR$^a$C(=O)NR$^a$R$^c$, NR$^a$(SO$_2$C$_{1-4}$alkyl), N(SO$_2$C$_{1-4}$alkyl)$_2$, OR$^a$, NR$^a$C(=O)C$_{1-4}$alkyleneN(R$^b$)$_2$, NR$^a$C(=O)C$_{1-4}$alkyleneC(=O)OR$^a$, NR$^a$(C=O)C$_{1-3}$alkylenearyl, NR$^a$C(=O)C$_{1-3}$alkyleneC$_{3-8}$heterocycloalkyl, NR$^a$C(=O)C$_{1-3}$alkyleneHet, and C(=O)NR$^a$SO$_2$R$^b$;

$R^4$ is selected from the group consisting of hydrogen, $C_{1-6}$alkyl, aryl, heteroaryl, aryl$C_{1-3}$alkyl, $C_{1-3}$alkylenearyl, $C_{1-3}$alkyleneHet, $C_{3-8}$cycloalkyl, and $C_{3-8}$heterocycloalkyl;

$R^a$ is selected from the group consisting of hydrogen, $C_{1-6}$alkyl, $C_{3-6}$cycloalkyl, aryl, aryl$C_{1-3}$alkyl, $C_{1-3}$alkylenearyl, heteroaryl, heteroaryl$C_{1-3}$alkyl, and $C_{1-3}$alkyleneheteroaryl;

$R^b$ is selected from the group consisting of hydrogen, $C_{1-6}$alkyl, $C_{3-8}$cycloalkyl, $C_{1-3}$alkyleneN(R$^a$)$_2$, aryl, aryl$C_{1-3}$alkyl, $C_{1-3}$alkylenearyl, and heteroaryl;

$R^c$ is selected from the group consisting of hydrogen, $C_{1-6}$alkyl, aryl, heteroaryl, aryl$C_{1-3}$alkyl, heteroaryl$C_{1-3}$alkyl, $C_{1-3}$alkyleneN(R$^a$)$_2$, $C_{1-6}$alkylenearyl, $C_{1-6}$alkyleneHet, halo$C_{1-6}$alkyl, $C_{3-8}$cycloalkyl, $C_{3-8}$heterocycloalkyl, Het, $C_{1-3}$alkyleneheteroaryl, $C_{1-6}$alkyleneC(=O)OR$^a$, and $C_{1-3}$alkyleneC$_{3-8}$heterocycloalkyl;

or $R^a$ and $R^c$ are taken together to form a 5- or 6-membered ring, optionally containing at least one heteroatom;

Q is O, S, or NR$^h$;

B is O, S, or NR$^h$;

C is O, S, or NR$^a$;

D is CR$^a$ or N;

E is CR$^a$, C(R$^a$)$_2$, or NR$^h$; and $R^h$ is null or is selected from the group consisting of hydrogen, $C_{1-6}$alkyl, aryl, heteroaryl, aryl$C_{1-3}$alkyl, heteroaryl$C_{1-3}$alkyl, $C_{1-3}$alkylenearyl, and $C_{1-3}$alkyleneheteroaryl;

Het represents a 5- or 6-membered heterocyclic ring, saturated or partially or fully unsaturated, containing at least one heteroatom selected from the group consisting of oxygen, nitrogen, and sulfur, and optionally substituted with $C_{1-4}$alkyl or C(=O)OR$^a$;

n is 0 or 1;

q is 0, 1, 2, 3, or 4;

t is 1, 2, 3, or 4;

and pharmaceutically acceptable salts and solvates thereof.

As used herein, the term "alkyl" includes straight chained and branched hydrocarbon groups containing the indicated number of carbon atoms, typically methyl, ethyl, propyl, and butyl groups. The hydrocarbon group can contain up to 16 carbon atoms. The term "alkyl" also includes "bridged alkyl," i.e., a $C_4$–$C_{16}$ bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. The term "cycloalkyl" is defined as a cyclic $C_3$–$C_8$ hydrocarbon group, e.g., cyclopropyl, cyclobutyl, cyclohexyl, and cyclopentyl.

The term "alkenyl" is defined identically as "alkyl," except for containing a carbon-carbon double bond. "Cycloalkenyl" is defined similarly to cycloalkyl, except a carbon-carbon double bond is present in the ring.

The term "alkylene" refers to an alkyl group having a substituent. For example, the term "$C_{1-3}$alkylenearyl" refers to an alkyl group containing one to three carbon atoms, and substituted with an aryl group. The term "alkenylene" as used herein is similarly defined, and contains the indicated number of carbon atoms and a carbon-carbon double bond, and includes straight chained and branched alkenylene groups, like ethyenylene.

The term "halo" or "halogen" is defined herein to include fluorine, bromine, chlorine, and iodine.

The term "haloalkyl" is defined herein as an alkyl group substituted with one or more halo substituents, either fluoro, chloro, bromo, iodo, or combinations thereof. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl. Unless otherwise indicated, an "aryl" group can be unsubstituted or substituted, for example, with one or more, and in particular one to three, halo, alkyl, hydroxyalkyl, alkoxy, alkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like. The terms "arylC$_{1-3}$alkyl" and "heteroarylC$_{1-3}$alkyl" are defined as an aryl or heteroaryl group having a C$_{1-3}$alkyl substituent.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "heterocycloalkyl" is defined as monocyclic, bicyclic, and tricyclic groups containing one or more, e.g., one to three, heteroatoms independently selected from the group consisting of oxygen, nitrogen, and sulfur. A "heterocycloalkyl" group also can contain an oxo group (=O) attached to the ring. Nonlimiting examples of heterocycloalkyl groups include 1,3-dioxolane, 2-pyrazoline, pyrazolidine, pyrrolidine, piperazine, a pyrroline, 2H-pyran, 4H-pyran, morpholine, thiopholine, piperidine, 1,4-dithiane, and 1,4-dioxane.

The term "hydroxy" is defined as —OH.

The term "alkoxy" is defined as —OR, wherein R is alkyl.

The term "alkoxyalkyl" is defined as an alkyl group wherein a hydrogen has been replaced by an alkoxy group. The term "(alkylthio)alkyl" is defined similarly as alkoxyalkyl, except a sulfur atom, rather than an oxygen atom, is present.

The term "hydroxyalkyl" is defined as a hydroxy group appended to an alkyl group.

The term "amino" is defined as —NH$_2$, and the term "alkylamino" is defined as —NR$_2$, wherein at least one R is alkyl and the second R is alkyl or hydrogen.

The term "acylamino" is defined as RC(=O)N, wherein R is alkyl or aryl.

The term "alkylthio" is defined as —SR, wherein R is alkyl.

The term "alkylsulfinyl" is defined as R—SO$_2$, wherein R is alkyl.

The term "alkylsulfonyl" is defined as R—SO$_3$, wherein R is alkyl.

The term "nitro" is defined as —NO$_2$.

The term "trifluoromethyl" is defined as —CF$_3$.

The term "trifluoromethoxyl" is defined as —OCF$_3$.

The term "spiro" as used herein refers to a group having two carbon atoms directly bonded to the carbon atom to which R$^1$ is attached.

The term "cyano" is defined as —CN.

In a preferred embodiment, q is 0. In other preferred embodiments, R$^0$ is selected from the group consisting of aryl, Het, OR$^a$, C(=O)OR$^a$, C$_{1-4}$alkyleneNR$^a$R$^b$, OC(=O)R$^a$, C(=O)R$^a$, NR$^a$R$^b$, C$_{3-8}$cycloalkyl, C$_{3-8}$cycloalkylQ, C(=O)NR$^a$R$^b$, and C(=O)NR$^a$R$^c$.

In a preferred group of compounds of formula (I), R$^1$ is represented by

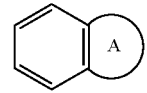

wherein the bicyclic ring can represent, for example, naphthalene or indene, or a heterocycle, such as benzoxazole, benzothiazole, benzisoxazole, benzimidazole, quinoline, indole, benzothiophene, or benzofuran, or

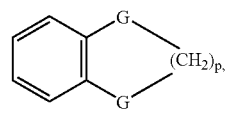

wherein p is an integer 1 or 2, and G, independently, is C(R$^a$)$_2$, O, S, or NR$^a$. The bicyclic ring comprising the R$^1$ substituent typically is attached to the rest of the molecule by a phenyl ring carbon atom.

In another preferred group of compounds of formula (I), R$^1$ is represented by an optionally substituted bicyclic ring

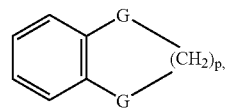

wherein p is 1 or 2, and G, independently, are C(R$^a$)$_2$ or O.

Especially preferred R$^1$ substituents include

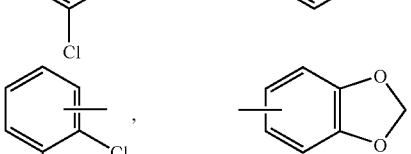

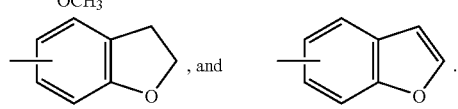

Within this particular group of compounds, nonlimiting examples of substituents for the bicyclic ring include halogen (e.g., chlorine), $C_{1-3}$alkyl (e.g., methyl, ethyl, or i-propyl), $OR^a$ (e.g., methoxy, ethoxy, or hydroxy), $CO_2R^a$, halomethyl or halomethoxy (e.g., trifluoromethyl or trifluoromethoxy), cyano, nitro, and $NR^aR^b$.

In other preferred embodiments, $R^1$ is optionally substituted and selected from the group consisting of $C_{1-4}$alkyleneQR$^a$, $C_{1-4}$alkyleneQC$_{1-4}$alkyleneQR$^a$, $C_{3-8}$cycloalkyl, $C_{3-8}$cycloalkenyl, $C_{1-6}$alkyl,

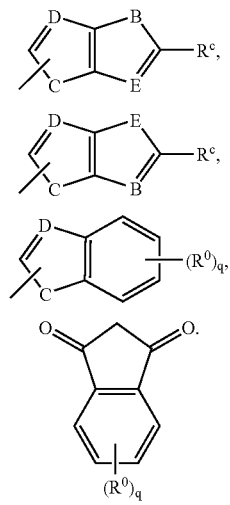

In a more preferred group of compounds of formula (I), $R^1$ is represented by

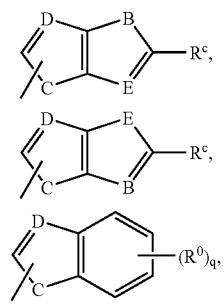

$C_{3-8}$cycloalkyl, $C_{3-8}$cycloalkenyl, $C_{1-6}$alkyl, $C_{1-4}$alkyleneQR$^a$, and $C_{1-4}$alkyleneQC$_{1-4}$alkyleneQR$^a$. A preferred Q is oxygen.

Some preferred $R^1$ substituents are

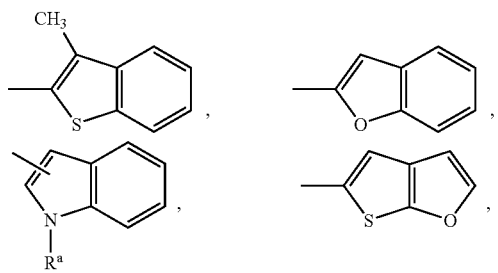

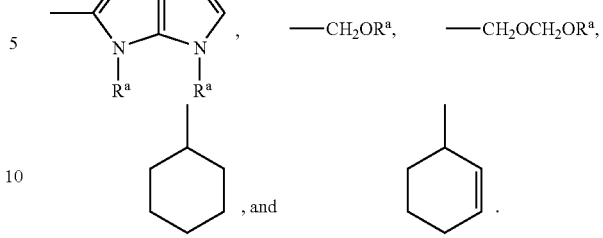

Within this particular group of compounds, preferred $R^a$ substituents include hydrogen, $C_{1-6}$alkyl, and benzyl.

In a preferred embodiment, $R^2$ is selected from the group consisting of hydrogen, aryl, heteroaryl, $OR^a$, $NR^aR^b$, $NR^aR^c$, $C_{1-4}$alkyleneHet, $C_{1-4}$alkyleneheteroaryl, $C_{1-4}$alkylenearyl, $C_{1-4}$alkyleneC(=O)C$_{1-4}$alkylenearyl, $C_{1-4}$alkyleneC(=O)OR$^a$, $C_{1-4}$alkyleneC(=O)NR$^a$R$^b$, $C_{1-4}$alkyleneC(=O)NR$^a$R$^c$, $C_{1-4}$alkyleneC(=O)Het, $C_{1-4}$alkyleneNR$^a$R$^b$, $C_{1-4}$alkyleneNR$^a$R$^c$, $C_{1-4}$alkyleneNR$^a$C(=O)R$^a$, and $C_{1-4}$alkyleneOC$_{1-4}$alkyleneOR$^a$.

In more preferred embodiments, $R^2$ is selected from the group consisting of hydrogen; $C_{1-4}$alkyleneheteroaryl, wherein the heteroaryl group is selected from the group consisting of benzimidazole, a triazole, and imidazole; $C_{1-4}$alkyleneHet, wherein Het is selected from the group consisting of piperazine, morpholine, pyrrolidine, pyrrolidone, tetrahydrofuran, piperidine,

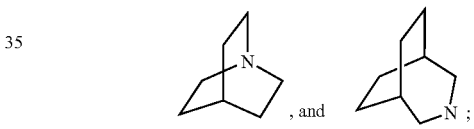

$C_{1-4}$alkyleneC$_6$H$_5$, optionally substituted with one to three groups selected from the group consisting of $C(=O)OR^a$, $NR^aR^b$, $NR^aSO_2CF_3$, $SO_2NR^aR^b$, CN, $OR^a$, $C(=O)R^a$, $C_{1-4}$alkyleneNR$^a$R$^b$, nitro, OC$_{1-4}$alkylenearyl, and OC$_{1-4}$alkyleneNR$^a$R$^b$; $C_{1-4}$alkyleneC(=O)benzyl; $C_{1-4}$alkyleneC(=O)OR$^a$; $C_{1-4}$alkyleneC(=O)NR$^a$R$^b$; $C_{1-4}$alkyleneC(=O)NR$^a$R$^c$; $C_{1-4}$alkyleneHet; $NR^aR^b$; OH; OC$_{1-4}$alkyl; $C_6H_5$; $C_{1-4}$alkyleneNR$^a$R$^b$; $C_{1-4}$alkyleneOR$^a$; $C_{1-4}$alkyleneNHC(=O)R$^a$; and $C_{1-4}$alkyleneOC$_{1-4}$alkyleneOR$^a$. In most preferred embodiments, $R^2$ is hydrogen.

In preferred embodiments, $R^3$ is selected from the group consisting of $C(=O)OR^a$, $C(=O)R^a$, $C(=O)NR^aC_{1-4}$alkyleneOC$_{1-6}$alkyl, $C(=O)NR^aC_{1-4}$alkyleneC$_{3-8}$cycloalkyl, $C(=O)$Het,

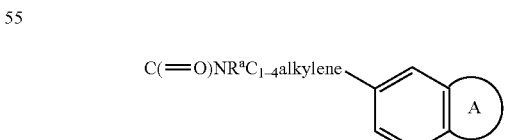

$C(=O)NR^aC_{1-4}$alkyleneheteroaryl, $C(=O)NR^aC_{1-4}$alkylenearyl, $C(=O)NR^aC_{1-4}$alkyleneHet, $C(=O)NR^aR^c$, and $C(=S)NR^aR^c$;

In preferred embodiments, $R^4$ is selected from the group consisting of hydrogen, $C_{1-6}$alkyl, aryl, and heteroaryl.

In preferred embodiments, n is 0, or X is selected from the group consisting of C(=O), C(=O)CR$^a$=CR$^a$, (CH$_2$)$_t$C=O, C(=S), and C(=N—OR$^a$).

In preferred embodiments, Y is selected from the group consisting of R$^a$, R$^d$, N(R$^b$)(CH$_2$)$_n$R$^c$, O(CH$_2$)$_n$R$^c$, N(R$^b$)C(=O)R$^c$, and N(R$^a$)C(=O)R$^c$.

In especially preferred embodiments, q is 0 or R$^0$ is selected from the group consisting of halo, methyl, trifluoromethyl, and trifluoromethyl; R$^1$ is selected from the group consisting of

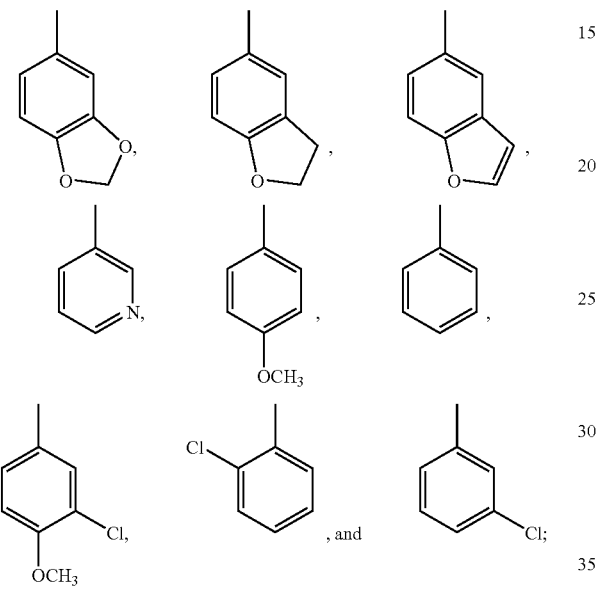

R$^2$ is selected from the group consisting of hydrogen, C$_{1-6}$alkyl, C(=O)NR$^a$R$^c$, and C$_{1-4}$alkyleneHet; R$^3$ is selected from the group consisting of C(=O)OC$_2$H$_5$, C(=O)OCH$_3$, C(=O)NHCH$_2$C$_6$H$_5$, C(=O)NH(CH$_2$)$_2$C$_6$H$_5$, C(=O)NHC$_6$H$_5$, C(=O)NH$_2$, C(=O)N(CH$_3$)$_2$, C(=S)N(CH$_3$)$_2$, C(=O)NH(CH$_2$)$_2$CH$_3$, C(=O)N(CH$_2$)$_3$CH$_3$, C(=O)NHCH$_3$, C(=O)NHCH(CH$_3$)$_2$, C(=O)NH(CH$_2$)$_3$OCH$_3$,

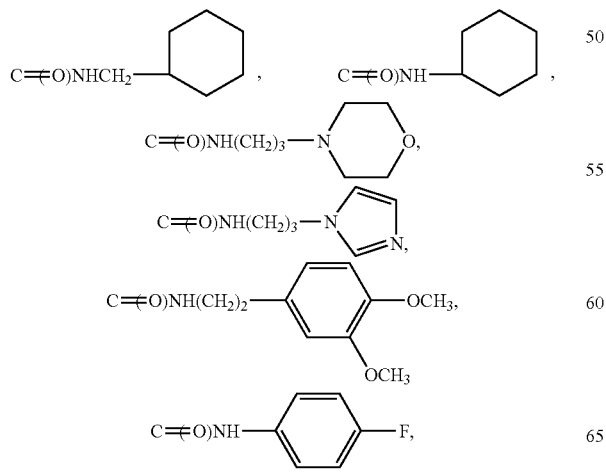

-continued

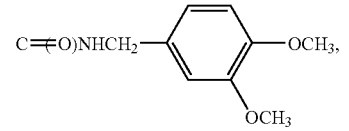
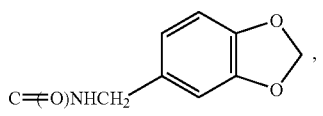
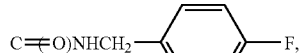
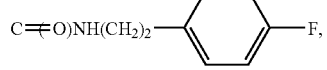
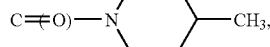
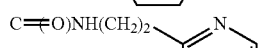
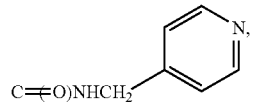
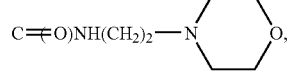
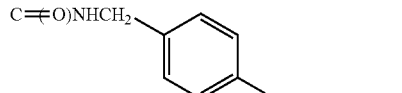
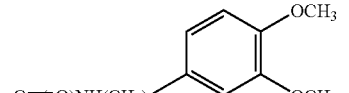
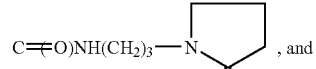
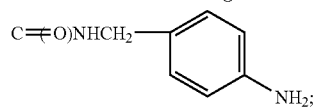
, and

R$^4$ is selected from the group consisting of hydrogen and C$_{1-6}$alkyl; X is selected from the group consisting of C(=O), C(=S), CH$_2$C(=O), and C(=O)CH=CH, or n is 0; and Y is selected from the group consisting of NH(CH$_2$)$_3$CH$_3$, OCH$_3$, C$_6$H$_5$, and

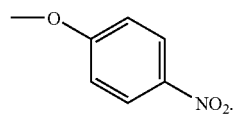

An especially preferred subclass of compounds within the general scope of formula (I) is represented by compounds of formula (II)

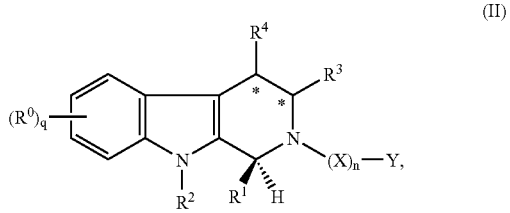

and pharmaceutically acceptable salts and solvates (e.g., hydrates) thereof.

Compounds of formula (I) can contain one or more asymmetric center, and, therefore, can exist as stereoisomers. The present invention includes both mixtures and separate individual stereoisomers of the compounds of formula (I). Compounds of formula (I) also can exist in tautomeric forms, and the invention includes both mixtures and separate individual tautomers thereof.

Pharmaceutically acceptable salts of the compounds of formula (I) can be acid addition salts formed with pharmaceutically acceptable acids. Examples of suitable salts include, but are not is limited to, the hydrochloride, hydrobromide, sulfate, bisulfate, phosphate, hydrogen phosphate, acetate, benzoate, succinate, fumarate, maleate, lactate, citrate, tartrate, gluconate, methanesulfonate, benzenesulfonate, and p-toluenesulfonate salts. The compounds of formula (I) also can provide pharmaceutically acceptable metal salts, in particular alkali metal salts and alkaline earth metal salts, with bases. Examples include the sodium, potassium, magnesium, and calcium salts.

Compounds of the present invention are potent and selective inhibitors of cGMP-specific PDE5. Thus, compounds of formula (I) are of interest for use in therapy, specifically for the treatment of a variety of conditions where selective inhibition of PDE5 is considered to be beneficial.

Phosphodiesterases (PDEs) catalyze the hydrolysis of cyclic nucleotides, such as cyclic adenosine monophosphate (cAMP) and cyclic guanosine monophosphate (cGMP). The PDEs have been classified into at least seven isoenzyme families and are present in many tissues (J. A. Beavo, *Physiol. Rev.*, 75, p. 725 (1995)).

PDE5 inhibition is a particularly attractive target. A potent and selective inhibitor of PDE5 provides vasodilating, relaxing, and diuretic effects, all of which are beneficial in the treatment of various disease states. Research in this area has led to several classes of inhibitors based on the cGMP basic structure (E. Sybertz et al., *Expert. Opin. Ther. Pat.*, 7, p. 631 (1997)).

The biochemical, physiological, and clinical effects of PDE5 inhibitors therefore suggest their utility in a variety of disease states in which modulation of smooth muscle, renal, hemostatic, inflammatory, and/or endocrine function is desirable. The compounds of formula (I), therefore, have utility in the treatment of a number of disorders, including stable, unstable, and variant (Prinzmetal) angina, hypertension, pulmonary hypertension, congestive heart failure, acute respiratory distress syndrome, acute and chronic renal failure, atherosclerosis, conditions of reduced blood vessel patency (e.g., postpercutaneous transluminal coronary or carotid angioplasty, or post-bypass surgery graft stenosis), peripheral vascular disease, vascular disorders, such as Raynaud's disease, thrombocythemia, inflammatory diseases, stroke, bronchitis, chronic asthma, allergic asthma, allergic rhinitis, glaucoma, osteoporosis, preterm labor, benign prostatic hypertrophy, peptic ulcer, male erectile dysfunction, female sexual dysfunction, and diseases characterized by disorders of gut motility (e.g., irritable bowel syndrome).

An especially important use is the treatment of male erectile dysfunction, which is one form of impotence and is a common medical problem. Impotence can be defined as a lack of power, in the male, to copulate, and can involve an inability to achieve penile erection or ejaculation, or both. The incidence of erectile dysfunction increases with age, with about 50% of men over the age of 40 suffering from some degree of erectile dysfunction.

In addition, a further important use is the treatment of female arousal disorder. Female arousal disorders are defined as a recurrent inability to attain or maintain an adequate lubrication/swelling response of sexual excitement until completion of sexual activity. The arousal response consists of vasocongestion in the pelvis, vaginal lubrication, and expansion and swelling of external genitalia.

It is envisioned, therefore, that compounds of formula (I) are useful in the treatment of male erectile dysfunction and female arousal disorder. Thus, the present invention concerns the use of compounds of formula (I), or a pharmaceutically acceptable salt thereof, or a pharmaceutical composition containing either entity, for the manufacture of a medicament for the curative or prophylactic treatment of erectile dysfunction in a male animal and arousal disorder in a female animal, including humans.

The term "treatment" includes preventing, lowering, stopping, or reversing the progression or severity of the condition or symptoms being treated. As such, the term "treatment" includes both medical therapeutic and/or prophylactic administration, as appropriate.

It also is understood that "a compound of formula (I)," or a physiologically acceptable salt or solvate thereof, can be administered as the neat compound, or as a pharmaceutical composition containing either entity.

Although the compounds of the invention are envisioned primarily for the treatment of sexual dysfunction in humans, such as male erectile dysfunction and female arousal disorder, they also can be used for the treatment of other disease states.

A further aspect of the present invention, therefore, is providing a compound of formula (I) for use in the treatment of stable, unstable, and variant (Prinzmetal) angina, hypertension, pulmonary hypertension, chronic obstructive pulmonary disease, congestive heart failure, acute respiratory distress syndrome, acute and chronic renal failure, atherosclerosis, conditions of reduced blood vessel patency (e.g., post-PTCA or post-bypass graft stenosis), peripheral vascular disease, vascular disorders such as Raynaud's disease, thrombocythemia, inflammatory diseases, prophylaxis of myocardial infarction, prophylaxis of stroke, stroke, bronchitis, chronic asthma, allergic asthma, allergic rhinitis, glaucoma, osteoporosis, preterm labor, benign prostatic hypertrophy, male and female erectile dysfunction, or diseases characterized by disorders of gut motility (e.g., IBS).

According to another aspect of the present invention, there is provided the use of a compound of formula (I) for the manufacture of a medicament for the treatment of the above-noted conditions and disorders.

In a further aspect, the present invention provides a method of treating the above-noted conditions and disorders in a human or nonhuman animal body which comprises administering to said body a therapeutically effective amount of a compound of formula (I).

Compounds of the invention can be administered by any suitable route, for example by oral, buccal, inhalation, sublingual, rectal, vaginal, transurethral, nasal, topical, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

Oral administration of a compound of the invention is the preferred route. Oral administration is the most convenient and avoids the disadvantages associated with other routes of administration. For patients suffering from a swallowing disorder or from impairment of drug absorption after oral administration, the drug can be administered parenterally, e.g., sublingually or buccally.

Compounds and pharmaceutical compositions suitable for use in the present invention include those wherein the active ingredient is administered in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a range of dosage for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

The amount of composition administered is dependent on the subject being treated, on the subject's weight, the severity of the affliction, the manner of administration, and the judgment of the prescribing physician.

Specifically, for administration to a human in the curative or prophylactic treatment of the conditions and disorders identified above, oral dosages of a compound of formula (I) generally are about 0.5 to about 1000 mg daily for an average adult patient (70 kg). Thus, for a typical adult patient, individual tablets or capsules contain 0.2 to 500 mg of active compound, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of this invention.

For human use, a compound of the formula (I) can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of compounds of formula (I) into preparations which can be used pharmaceutically.

These pharmaceutical compositions can be manufactured in a conventional manner, e.g., by conventional mixing, dissolving, granulating, dragee-making, levigating, emulsifying, encapsulating, entrapping, or lyophilizing processes. Proper formulation is dependent upon the route of administration chosen. When a therapeutically effective amount of a compound of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% compound of the present invention, and preferably from about 25% to about 90% compound of the present invention. When administered in liquid form, a liquid carrier such as water, petroleum, or oils of animal or plant origin can be added. The liquid form of the composition can further contain physiological saline solution, dextrose or other saccharide solutions, or glycols. When administered in liquid form, the composition contains about 0.5% to about 90% by weight of a compound of the present invention, and preferably about 1% to about 50% of a compound of the present invention.

When a therapeutically effective amount of a compound of the present invention is administered by intravenous, cutaneous, or subcutaneous injection, the composition is in the form of a pyrogenfree, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

For oral administration, the compounds can be formulated readily by combining a compound of formula (I) with pharmaceutically acceptable carriers well known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding a compound of formula (I) with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

For administration by inhalation, compounds of the present invention are conveniently delivered in the form of an aerosol spray presentation from pressurized packs or a nebulizer, with the use of a suitable propellant. In the case of a pressurized aerosol, the dosage unit can be determined by providing a valve to deliver a metered amount. Capsules and cartridges of, e.g., gelatin, for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the present invention also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Many of the compounds of the present invention can be provided as salts with pharmaceutically compatible counterions. Such pharmaceutically acceptable base addition salts are those salts that retain the biological effectiveness and properties of the free acids, and that are obtained by reaction with suitable inorganic or organic bases.

In particular, a compound of formula (I) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

For veterinary use, a compound of formula (I) or a nontoxic salt thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (I), together with a pharmaceutically acceptable diluent or carrier therefor. There is further provided by the present invention a process of preparing a pharmaceutical composition comprising a compound of formula (I), which process comprises mixing a compound of formula (I), together with a pharmaceutically acceptable diluent or carrier therefor.

In a particular embodiment, the invention includes a pharmaceutical composition for the curative or prophylactic treatment of erectile dysfunction in a male animal, or arousal disorder in a female animal, including humans, comprising a compound of formula (I) or a pharmaceutically acceptable salt thereof, together with a pharmaceutically acceptable diluent or carrier.

Compounds of formula (I) can be prepared by any suitable method known in the art, or by the following processes which form part of the present invention. In the methods below, $R^0$, $R^1$, $R^2$, $R^3$, and $R^4$, as well as $R^a$ through $R^h$, Q, B, C, D, E, X, and Y, are defined as in structural formula (I) above. In particular, compounds of structural formula (I) can be prepared according to the following synthetic scheme.

Daugan U.S. Pat. No. 5,859,006, incorporated herein by reference, discloses preparation of a compound of structural formula (III):

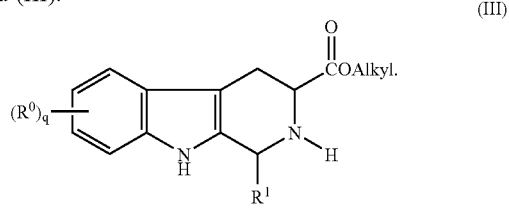

The compounds of structural formula (I) can be prepared from compounds similar to the compound of structural formula (III) using appropriate $R^2$ and $R^4$ substituents.

The following illustrates a general method of synthesizing a compound of structural formula (I).

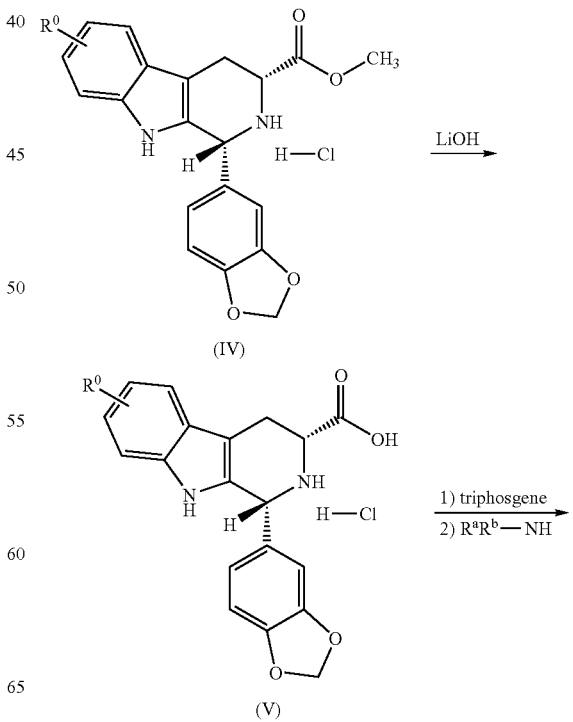

-continued

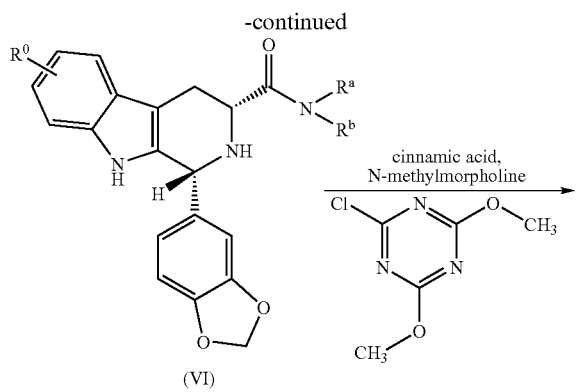
(VI)

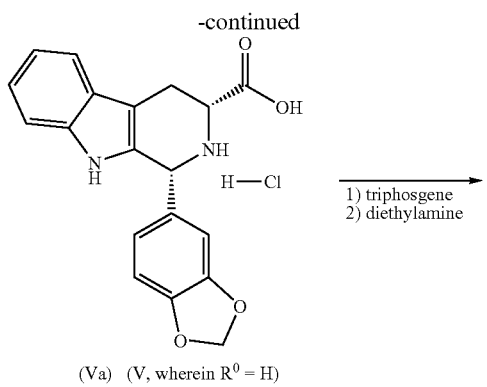
(Va) (V, wherein $R^0$ = H)

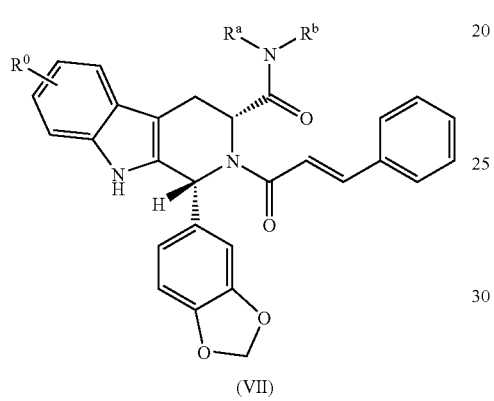
(VII)

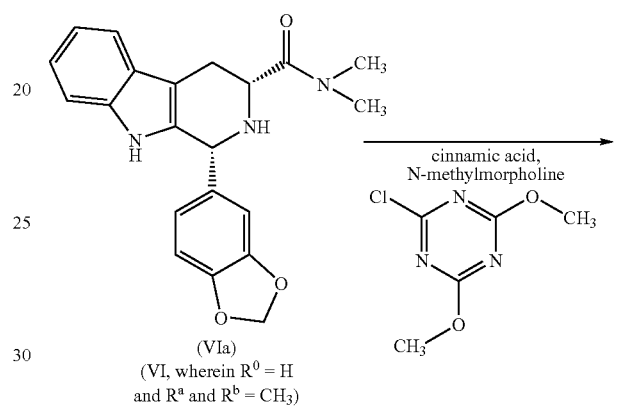
(VIa)
(VI, wherein $R^0$ = H
and $R^a$ and $R^b$ = $CH_3$)

Known compound (IV) (see Daugan U.S. Pat. No. 5,859,006) is hydrolyzed to carboxylic acid (V), which then is treated with triphosgene followed by treatment with a desired amine to provide amide (VI). Amide (VI) then is treated with a carboxylic acid in the presence of an activating group, or other carboxylic acid derivative (e.g., acid chloride), having the desired —(X)$_n$—Y residue and a base to provide bisamide (VII). Bisamide (VII) is a compound of structural formula (I).

The following illustrates a synthesis of compounds (V)–(VII) from compound (IV), wherein $R^0$ is hydrogen. The synthesis of compound (IV) can be found in Daugan U.S. Pat. No. 5,859,006.

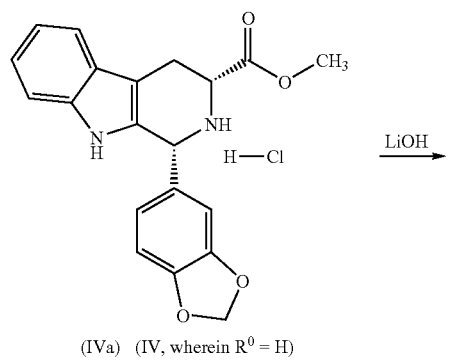
(IVa) (IV, wherein $R^0$ = H)

(VIIa)
(VII, wherein $R^0$ = H and $R^a$ and $R^b$ = $CH_3$)

Preparation of (1R,3R)-1-benzo[1,3]dioxol-5-yl-2,3,4,9-tetrahydro-1H-β-carboline-3-carboxylic acid hydrochloride (Va)

Lithium hydroxide (0.32 g, 13.2 mmol) was added to a stirred mixture of (1R,3R)-1-benzo[1,3]dioxol-5-yl-2,3,4,9-tetrahydro-1H-β-carboline-3-carboxylic acid methyl ester (IVa) (2.5 g, 6.5 mmol) in 10 mL of anhydrous tetrahydrofuran at room temperature. Methanol (1 mL) was added to help dissolution of the solids. After stirring overnight at room temperature, the reaction mixture was partitioned between ethyl acetate (10 mL) and deionized water (25 mL). The layers were separated, and the pH of the aqueous layer was adjusted to 2.3 with 1 M HCl. After 1 hour, the resulting slurry was filtered, then the filter cake was washed with a quantity of deionized water sufficient to remove the yellow color. The resulting solid was dried under vacuum to give 1.38 g (57%) of compound (Va) as an off-white solid.

$^1$H NMR (DMSO-d$_6$) δ: 10.70 (s, 1H), 7.52 (d, J=7 Hz, 1H), 7.28 (d, J=8 Hz, 1H), 7.13–7.01 (m, 5H), 6.07 (s, 2H), 5.78 (s, 1H), 4.22 (dd, J=5, 11 Hz, 1H), 3.38 (dd, J=5, 15 Hz, 1H), 3.21 (dd, J=2, 15 Hz, 1H); MS ES+m/e 337 (p+1), ES−m/e 335 (p−1); IR (KBr, cm$^{-1}$) 3621, 3450, 1758.

Preparation of (1R,3R)-1-benzo[1,3]dioxol-5-yl-2-(3-phenyl-acryloyl)-2,3,4,9-tetrahydro-1H-β-carboline-3-carboxylic acid dimethylamide (VIa)

Triethylamine (1.5 mL, 10.7 mmol) was added to a stirred mixture of compound (Va) (2 g, 5.4 mmol) and 60 mL of anhydrous tetrahydrofuran at room temperature. Triphosgene (1.6 g, 5.4 mmol) was added to the slurry, then stirring was continued for 2 hours at room temperature. Dimethylamine was condensed into a dropping funnel (about 1 mL), and was added directly to the stirred slurry. After 1 hour, the reaction mixture was filtered and the volatiles were removed from the filtrate under vacuum. The resulting foam was subjected to flash chromatography (silica, EtOAc) to give a 1.65 g (86%) of compound (VIa) as a yellow foam.

$^1$H NMR (DMSO-d$_6$) δ: 10.38 (s, 1H), 7.44 (d, J=6 Hz, 1H), 7.21 (d, J=7 Hz, 1H), 7.03–6.88 (m, 3H), 6.83–6.79 (m, 2H), 5.99 (s, 2H), 5.13 (d, J=7 Hz, 1H), 4.04 (m, 1H), 3.12 (s, 3H), 2.86 (s, 3H), 2.8–2.76 (m, 2H); MS ES+m/e 364 (p+1), ES−m/e 362 (p−1); IR (KBr, cm$^{-1}$) 3463, 1642.

Preparation of (1R,3R)-1-benzo[1,3]dioxol-5-yl-2-(3-phenylacryloyl)-2,3,4,9-tetrahydro-1H-β-carboline-3-carboxylic acid dimethylamide (VIIa)

2-Chloro-3,5-dimethyoxy-2,4,6-triazine (0.5 g, 2.8 mmol) was added to a mixture of transcinnamic acid in 15 mL of anhydrous tetrahydrofuran. N-Methylmorpholine (0.32 mL, 2.9 mmol) was added and the resulting solution was stirred at room temperature for 1.75 hours. Compound (VIa) was added, then the reaction was stirred for 4 hours at room temperature. The reaction mixture was partitioned between ethyl acetate (25 mL) and 1 M HCl (25 mL). The layers were separated, and the organic layer was washed with 25 mL of saturated sodium bicarbonate solution followed by 25 mL of brine. The EtOAc was dried over MgSO$_4$, filtered, and removed under vacuum to give the crude product as a yellow foam. The product was purified by flash chromatography (50% hexane, 50% CH$_2$Cl$_2$ to CH$_2$Cl$_2$ to EtOAc) to yield 0.613 g (42%) of compound (VIIa) as a yellow foam: mp 175–178° C.

$^1$H NMR (DMSO-d$_6$) δ: 10.82, 10.75 (overlapping br s, 1H), 7.89–7.21 (m, 9H), 7.11–6.67 (m, 5H), 6.65 (br s, 1H), 5.92 (s, 2H), 5.70–5.63 (m, 1H), 2.9 (dd, J=6, 15 Hz, 1H), 2.75 (br s, 1H), 2.58 (br s, 2H), 2.51–2.48 (m, 1H), 2.36 (br s, 2H), 2.18 (br s, 1H); MS ES−m/e 492 (p−1).

The following scheme illustrates the synthesis of a compound of structural formula (I) from ester (IV), and illustrates an alternative method of synthesizing a bisamide (VII).

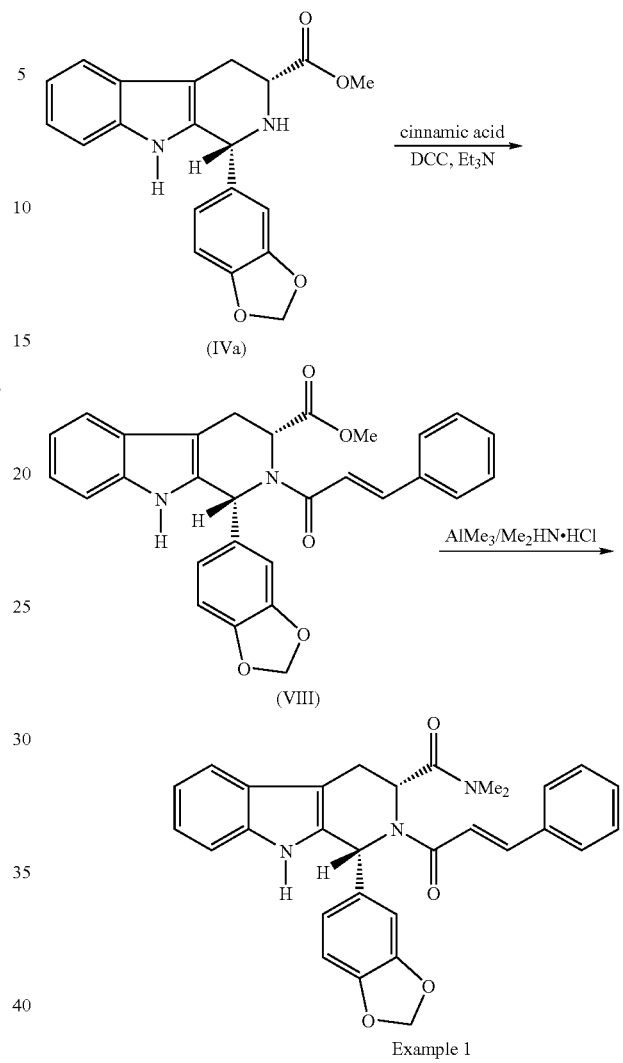

Example 1

The above scheme illustrates the synthesis of a compound of structural formula (II), i.e., compound (VIII), directly from compound (IVa) by reaction with a carboxylic acid having the desired (X)$_n$—Y residue, in the presence of dicyclohexylcarbodiimide and triethylamine. Compound (VIII) then can be converted to another compound of structural formula (I), i.e., Example 1, by a reaction using trimethyl aluminum and dimethylamine hydrochloride. The reaction between compound (IVa) and cinnamic acid is set forth in Bombrun U.S. Pat. No. 6,117,881, incorporated in its entirety herein by reference.

It should be understood that protecting groups can be utilized in accordance with general principles of synthetic organic chemistry to provide compounds of structural formula (I). Protecting group-forming reagents, like benzyl chloroformate and trichloroethyl chloroformate, are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of structural formula (I) not specifically exemplified herein can be prepared by persons skilled in the art.

In addition, compounds of formula (I) can be converted to other compounds of formula (I). Thus, for example, a particular R substituent can be interconverted to prepare another suitably substituted compound of formula (I). Examples of appropriate interconversions include, but are not limited to, OR$^a$ to hydroxy by suitable means (e.g., using a agent such as BBr$_3$, or a palladium catalyst, like palladium-on-carbon, and hydrogen), or amino to substituted amino, such as acylamino or sulphonylamino, using standard acylating or sulfonylating conditions.

Compounds of formula (I) can be prepared by the method above as individual stereoisomers or as a racemic mixture. Individual stereoisomers of the compounds of the invention can be prepared from racemates by resolution using methods known in the art for the separation of racemic mixtures into their constituent stereoisomers, for example, using HPLC on a chiral column, such as Hypersil naphthyl urea, or using separation of salts of stereoisomers. Compounds of the invention can be isolated in association with solvent molecules by crystallization from, or evaporation of, an appropriate solvent.

The pharmaceutically acceptable acid addition salts of the compounds of formula (I) that contain a basic center can be prepared in a conventional manner. For example, a solution of the free base can be treated with a suitable acid, either neat or in a suitable solution, and the resulting salt isolated either by filtration or by evaporation under vacuum of the reaction solvent. Pharmaceutically acceptable base addition salts can be obtained in an analogous manner by treating a solution of a compound of formula (I) with a suitable base. Both types of salt can be formed or interconverted using ion-exchange resin techniques. Thus, according to a further aspect of the invention, a method for preparing a compound of formula (I) or a salt or solvate (e.g., hydrate) is provided, followed by (i) salt formation, or (ii) solvate (e.g., hydrate) formation.

The following additional abbreviations are used hereafter in the accompanying examples: rt (room temperature), min (minute), h (hour), g (gram), mmol (millimole), m.p. (melting point), LiOH (lithium hydroxide), eq (equivalents), L (liter), mL (milliliter), μL (microliter), DMSO (dimethyl sulfoxide), Et$_3$N (triethylamine), MeNH$_2$ (methylamine), THF (tetrahydrofuran), Me$_2$NH (dimethylamine), DCC (1,3-dicyclohexylcarbodiimide), AlMe$_3$ (trimethylaluminum), Me (methyl), EtOAc (ethyl acetate), CHCl$_3$ (chloroform), and Na$_2$SO$_4$ (sodium sulfate).

Example 2 was prepared from Compound (IVa) by the following synthetic sequence.

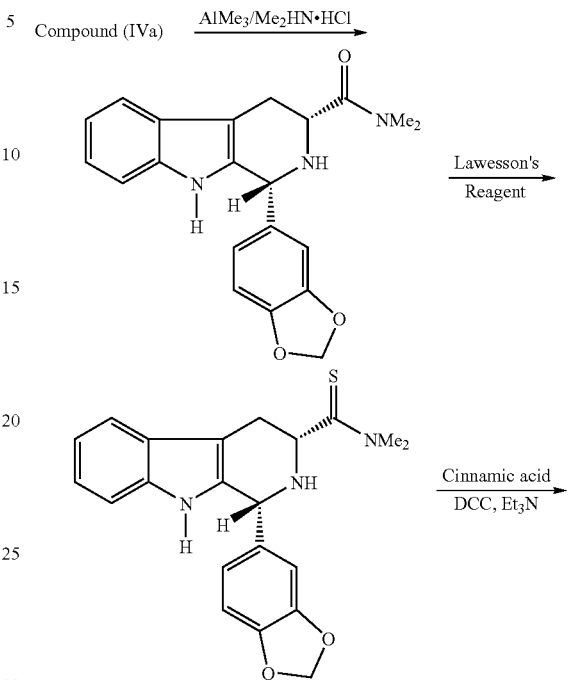

Example 2

EXAMPLE 3

(−)-(1R,3R)-1-Benzo[1,3]dioxol-5-yl-1,3,4,9-tetrahydro-beta-carboline-2,3-dicarboxylic acid 3-methyl ester 2-(4-nitrophenyl)ester

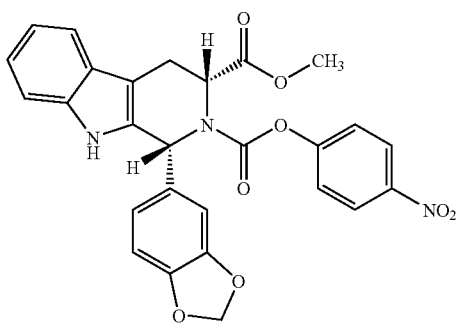

Example 3 was prepared from Compound (IVa) as follows. Also see F. Pinnen et al., *J. Chem. Soc., Perkin Trans. I*, 12, p. 1611 (1994).

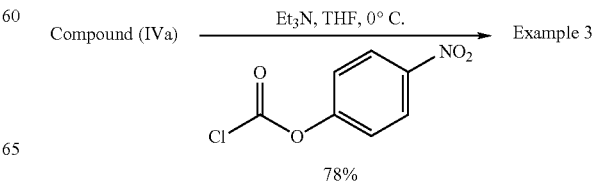

78%

4-Nitrophenyl chloroformate was added dropwise to a suspension of Compound (IVa) (2.0 g, 52 mmol) and Et₃N (1.8 mL, 13 mmol) in THF (50 mL) at 0° C. under a nitrogen blanket. The resulting mixture was slowly warmed to room temperature and stirred for 18 hours, then diluted with EtOAc (200 mL). The resulting solution was washed with brine (100 mL), dried over Na₂SO₄, filtered, and the solvents were removed under reduced pressure. The residue was purified by flash column chromatography, eluting with EtOAc/CHCl₃ (1:19) to provide Example 3 as a yellow powder (2.08 g, 78%): mp 175–187° C.; TLC R$_f$ (9:1 CHCl₃/EtOAc)=0.84.

¹H NMR (300 MHz, DMSO-d₆) δ: 10.90 (s, 1H), 8.33 (d, J=9.0 Hz, 2H), 7.58–7.56 (m, 3H), 7.30 (d, J=7.7 Hz, 1H), 7.07 (dt, J=6.5, 21.8 Hz, 2H), 6.88 (bs, 1H), 6.72 (s, 1H), 6.58 (bs, 1H), 6.44 (bs, 1H), 6.01 (s, 2H), 5.70 (bs, 1H), 5.45 (bs, 1H), 3.40 (d, J=13.7 Hz, 1H), 3.28–3.21 (m, 1H); API MS m/z 516 [C₂₇H₂₁N₃O₈+H]⁺; [α]$_D^{25° C.}$=−121.7° (c=1.0, DMSO). Anal. Calcd. for C₂₇H₂₁N₃O₈: C, 62.91; H, 4.11; N, 8.15. Found: C, 62.54; H, 3.91; N, 8.02.

The following Examples 4–12 were prepared in a manner similar to Examples 1–3.

Example 4

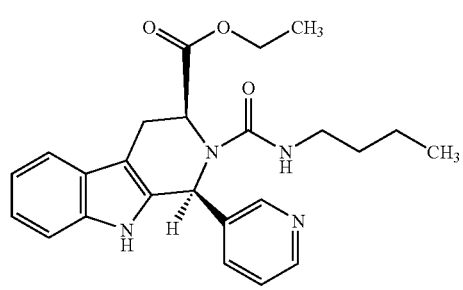

Example 5

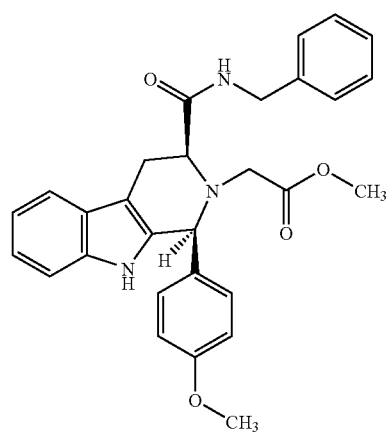

Example 6

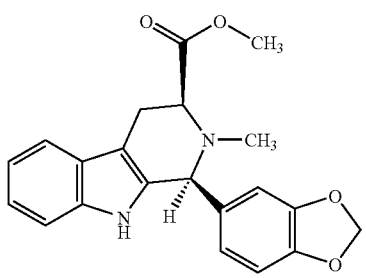

Example 7

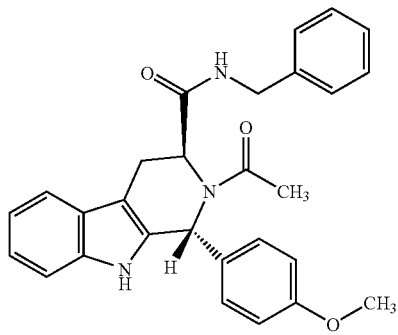

Preparation of Example 8

Example 8

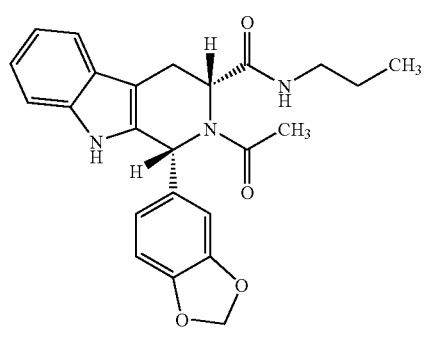

Example 8 was prepared by the following synthetic sequence

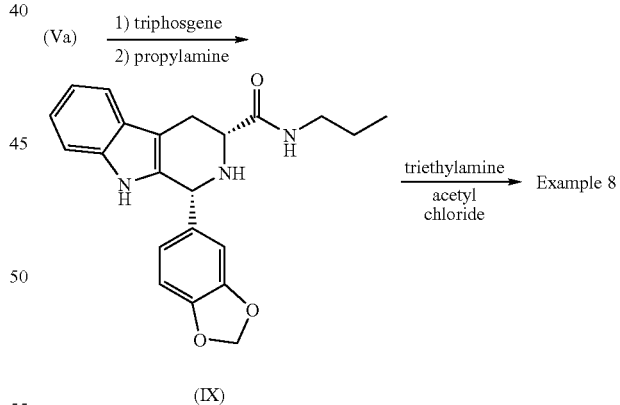

Preparation of (1R)-(+)-1-benzo[1,3]dioxol-5-yl-2,3,4,9-tetrahydro-1H-β-carboline-3-carboxylic acid propylamide (Compound (IX))

A suspension of compound (Va) (2.0 g, 6.0 mmol) and triethylamine (2 mL) in tetrahydrofuran (50 mL) was immersed in a sonicator until all solids dissolved. Triphosgene (1.6 g, 5.4 mmol) was added, and the resulting suspension was stirred for 6 hours without cooling. A colorless solid was removed by filtration, then the filtrate was concentrated to a foam. The foam was dissolved in chloroform (50 mL) and n-propylamine (2 mL) was added. The reaction was stirred for 18 hours without cooling, the solvent was evaporated, and the residue purified by chromatography (silica gel, 75% ethyl acetate: 25% hexanes) to give 1.4 g (61%) of compound (IX) as a solid.

$^1$H NMR (DMSO-$d_6$) δ: 10.71 (s, 1H), 7.84 (t, J=8 Hz, 1H), 7.45–6.59 (m, 7H), 6.0 (s, 2H), 5.15 (s, 1H), 3.45 (m, 1H), 3.04 (q, J=8 Hz, 2H), 2.8 (dd, J=5, 13 Hz, 1H), 1.4 (m, 2H), 0.84 (t, J=8 Hz, 3H); MS ES+m/e 378.2 (p+1), ES−m/e 376.2 (p−1); Anal. Calcd. for $C_{22}H_{23}N_3O_3$; C, 70.01; H, 6.14; N, 11.13. Found: C, 70.30; H, 6.23; N, 11.27.

Preparation of (1R)-(+)-2-acetyl-1-benzo[1,3]dioxol-5-yl-2,3,4,9-tetrahydro-1H-β-carboline-3-carboxylic acid propylamide (Example 8)

To a solution of compound (IX) (1.4 g, 3.7 mmol) and triethylamine (2 mL) in methylene chloride (25 mL) was added acetyl chloride (0.36 mL, 5.0 mmol), then the mixture was stirred for 18 hours at room temperature. The solution was washed once with water, once with saturated sodium chloride solution, dried (sodium sulfate), filtered, and concentrated in vacuo to provide a solid that was recrystallized (ethyl acetate) to give 310 mg (20%) of Example 8 as a solid: mp 163–165° C.

$^1$H NMR (DMSO-$d_6$) δ: 10.88 (s, 1H), 7.95 (t, J=5 Hz, 0.6H (rotamer)), 7.7 (t, J=5 Hz, 0.4H (rotamer)), 7.4–6.7 (m, 7H), 5.85–6.2 (m, 3H), 5.25 (br s, 0.6H (rotamer)), 4.95 (br s, 0.4 H (rotamer)), 3.35 (dd, J=6, 13 Hz, 2H), 2.85 (m, 2H), 2.0 (s, 1.8H (rotamer)), 1.9 (s, 1.2H (rotamer)), 1.2 (m, 2H), 0.62 (m, 3H); MS ES+m/e 420.2 (p+1), ES−m/e 418.3 (p−1); Anal. Calcd. for $C_{24}H_{25}N_3O_4$: C, 68.71; H, 6.01; N, 10.02. Found: C, 68.57; H, 5.69; N, 10.02.

Preparation of Example 9

Example 9

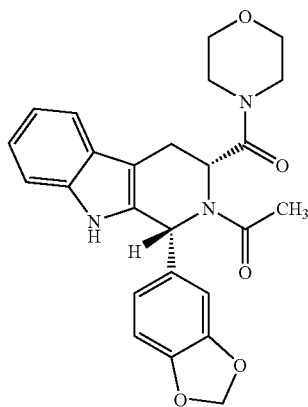

Example 9 was prepared by the following synthetic sequence:

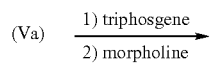

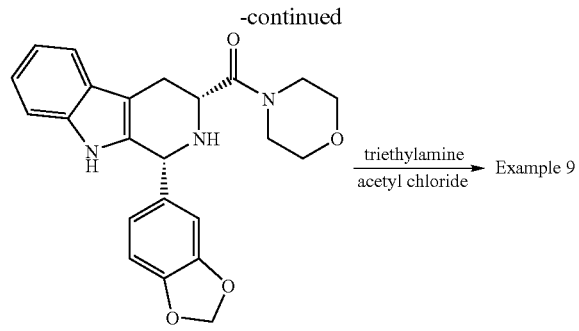

(X)

Preparation of (1R)-(+)-(1-benzo[1,3]dioxol-5-yl-2,3,4,9-tetrahydro-1H-β-carbolin-3-yl)-moroholine-4-yl-methanone (X)

A suspension of compound (Va) (350 mg, 1.04 mmol) and triethylamine (0.5 mL) in tetrahydrofuran (10 mL) was sonicated until all solids were dissolved. Triphosgene (300 mg, 1.0 mmol) was added and the resulting suspension was stirred for 2 hours. A colorless solid was removed by filtration and the filtrate was concentrated in vacuo to provide a foam. The foam was dissolved in methylene chloride (15 mL), treated with morpholine (0.5 mL), and the resulting solution stirred for 18 hours. The solvent was evaporated in vacuo, and the crude material was purified by chromatography (silica gel, ethyl acetate) to give 280 mg (66%) of compound (X) as a solid.

$^1$H NMR (DMSO-$d_6$) δ: 10.35 (s, 1H), 7.45–6.77 (m, 7H), 6.02 (s, 2H), 5.15 (s, 1H), 4.06 (dd, J=4, 13 Hz), 3.7–3.45 (m, 8H), 2.85 (dd, J=4, 13 Hz, 2H), 2.1 (t, J=10 Hz, 1H); MS ES+m/e 406.0 (p+1), ES−m/e 404.2 (p−1).

Preparation of (1R)-(+)-1-[benzo[1,3]dioxol-5-yl-3-(morpholine-4-carbonyl)-1,3,4,9-tetrahydro-β-carbolin-2-yl]-ethanone (Example 11)

To a solution of compound (X) (1.7 g, 4.2 mmol) and triethylamine (2 mL) in methylene chloride (50 mL) was added acetyl chloride (3.29 mg, 4.2 mmol, 0.3 mL). The reaction was stirred for 18 hours without cooling. An additional quantity of acetyl chloride (0.1 mL) was added, and stirring was continued for 30 minutes. The reaction was concentrated and purified by chromatography (silica gel, 75% ethyl acetate: 25% hexanes, then ethyl acetate) to give 800 mg (42%) of Example 9 as a colorless solid.

$^1$H NMR (DMSO-$d_6$) δ: 10.8 (s, 1H), 7.55–6.8 (m, 7H), 6.75 (br s, 0.6H (rotamer)), 6.62 (br s, 0.4H (rotamer)), 5.97 (d, J=4 Hz, 2H), 5.6 (br s, 0.6H (rotamer)), 5.75 (br s, 0.4H (rotamer)), 3.54–2.95 (m, 9H), 2.85 (dd, J=5, 13 Hz, 1H), 2.3 (s, 3H); MS ES+m/e 448.1 (p+1), ES−m/e 446.2 (p−1); Anal. Calcd. for $C_{25}H_{25}N_3O_5$: C, 67.10; H, 5.63; N, 9.39. Found: C, 67.00; H, 5.69; N, 9.28.

Example 10

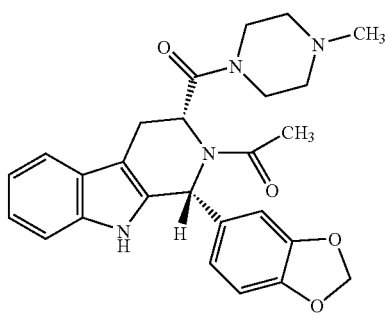

Preparation of Example 11

Example 11

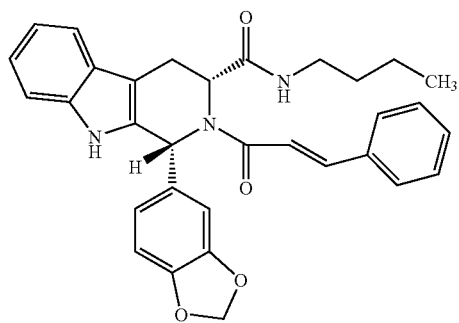

Example 11 was prepared using the following synthetic sequence:

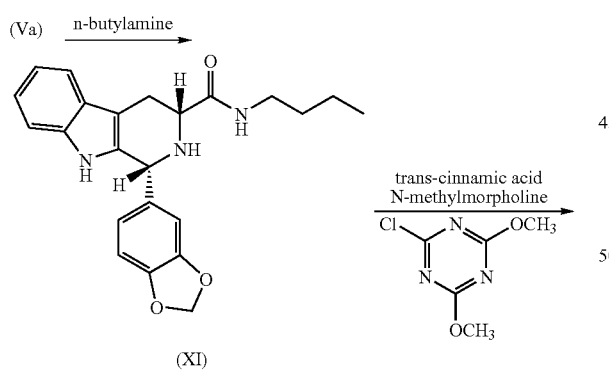

Preparation of (1R,3R)-(+)-1-benzo[1,3]dioxol-5-yl-2,3,4,9-tetrahydro-1H-β-carboline-3-carboxylic acid butylamide (XI)

To a solution of compound (Va) (2.17 9, 6 mmol) in chloroform (50 mL) was added n-butylamine (585 mg, 6 mmol). The reaction was stirred for 18 hours at room temperature. The solvent was concentrated in vacuo, then the residue was purified by chromatography (silica gel, 50% ethyl acetate: 70% hexanes) to give 1.7 g (72%) of compound (XI) as a colorless foam.

$^1$H NMR (DMSO-$d_6$) δ: 10.28 (s, 1H), 7.6 (t, J=6 Hz, 1H), 7.45–6.85 (m, 8H), 6.0 (s, 2H), 5.08 (d, J=7 Hz, 1H), 3.55 (m, 1H), 3.14 (q, J=6 Hz, 2H), 2.97 (dd, J=3, 16 Hz, 1H), 2.7 (dt, J=3,16 Hz), 1.47 (m, 2H), 1.3 (m, 2H), 0.82 (t, J=6 Hz, 3H); MS ES+m/e 392.3 (p+1), ES−m/e 390.4 (p−1); Anal. Calcd. for $C_{23}H_{25}N_3O_3$: C, 70.57; H, 6.43; N, 10.73. Found: C, 70.34; H, 6.11; N, 10.53.

Preparation of (1R,3R)-(+)-1-benzo[1,3]dioxol-5-yl-2-(3-phenylacryloyl)-2,3,4,9-tetrahydro-1H-β-carboline-3-carboxylic acid butylamide (Example 11)

A mixture of trans-cinnamic acid (376 mg. 2.5 mmol), 2-chloro-3,5-dimethoxy-2,4,6-triazine (500 mg, 2.8 mmol), N-methylmorpholine (0.32 mL, 2.9 mmol), and tetrahydrofuran (20 mL) was stirred without cooling for 1.5 hours. Compound (XI) (1.0 g, 2.5 mmol) was added, then the reaction was stirred for an additional 18 hours. The solvent was evaporated, and the residue was dissolved in ethyl acetate, washed once with 1N hydrochloric acid, once with saturated sodium bicarbonate solution, dried (sodium sulfate), filtered, and concentrated in vacuo. Chromatography (silica gel, 30% ethyl acetate: 70% hexanes) of the residue provided 800 mg (61%) of Example 11 as a solid: mp 114–117° C.

$^1$H NMR (DMSO-$d_6$) δ: 10.8 (s, 1H), 6.8–7.7 (m, 14H), 5.95 (s, 2H), 5.3 (m, 1H), 3.0 (m, 1H), 2.78 (m, 1H), 1.15 (m, 6H), 0.8 (m, 3H); MS ES+m/e 522.02 (p+1), ES−m/e 520.13 (p−1), IR (KBr, cm$^{-1}$) 1674, 1644, 1503, 1487; Anal. Calcd. for $C_{32}H_{31}N_3O_4$: C, 73.68; H, 5.99; N, 8.06. Found: C, 73.33; H, 5.96; N, 8.25.

Preparation of Example 12

Example 12

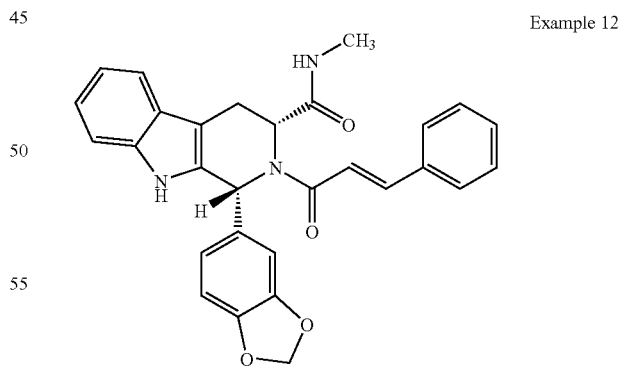

Example 12 was prepared using the following synthetic sequence:

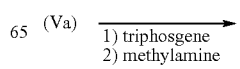

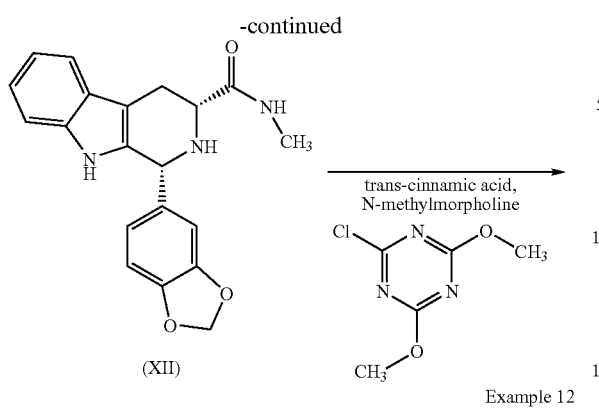

Example 12

Preparation of (1R,3R)-1-benzo[1,3]dioxol-5-yl-2-(3-phenylacryloyl)-2,3,4,9-tetrahydro-1H-β-carboline-3-carboxylic acid methylamide (XII)

Triethylamine (2 mL, 14 mm, 2.4 eq) was added to a stirred mixture of compound (Va) (2 g, 5.2 mmol) and anhydrous tetrahydrofuran (25 mL) at room temperature. The resulting mixture was sonicated until complete dissolution was achieved. Triphosgene (1.6 g, 5.4 mmol) was added to the slurry, and stirring was continued for 5 hours at room temperature. The solids were removed by filtration and the filtrate concentrated in vacuo. The residue was dissolved in chloroform, and a solution of 2 M methylamine in tetrahydrofuran (10 mL, 20 mmol) was added. After 1.5 hours, the reaction mixture was diluted with water and shaken. The organic layer was dried (sodium sulfate), filtered, and concentrated in vacuo. The residue (compound (XII) was used as is.

$^1$H NMR (DMSO-d$_6$) δ: 10.38 (s, 1H), 7.44 (d, J=6 Hz, 1H), 7.21 (d, J=7 Hz, 1H), 7.03–6.88 (m, 3H), 6.83–6.79 (m, 2H), 5.99 (s, 2H), 5.10 (m, 1H), 3.5–3.6 (m, 1H), 3.30 (s, 3H), 3.00 (dd, J=1.5, 11.4 Hz, 1H), 2.72 (dd, J=2.5, 11.3 Hz, 1H), 2.64 (s, 3H), 2.49 (s, 3H); MS ES+m/e 350.2 (p+1), ES-348.2 (p-1).

Preparation of (1R,3R)-{2-[(2E)-3-(phenyl)prop-2-enoyl]-1-(2H-benzo[d]1,3-dioxolan-5-yl-(1,2,3,4-tetrahydrobetacarbolin-3-yl)}-N-methylcarboxamide (Example 12)

2-Chloro-3,5-dimethoxy-2,4,6-triazine (0.5 g, 2.8 mmol) was added to a solution of transcinnamic acid (0.376 g, 2.5 mmol) in anhydrous tetrahydrofuran (20 mL). N-Methylmorpholine (0.32 mL, 2.9 mmol) was added, then the resulting solution was stirred at room temperature for 1.5 hours. A solution of compound (XII) (0.873 g, 2.50 mmol) in anhydrous tetrahydrofuran (5 mL) was added, and the reaction was stirred for 2 hours at room temperature. The reaction mixture was partitioned between ethyl acetate and 1M hydrochloric acid. The layers were separated, and the organic layer was washed once with saturated sodium bicarbonate solution and once with saturated sodium chloride solution. The organic layer was dried (sodium sulfate), filtered, and concentrated in vacuo to give the crude product as a yellow foam. The product was purified by flash chromatography (silica gel, 50% hexane/50% ethyl acetate to ethyl acetate) to provide 0.43 g (35%) of Example 12 as a yellow foam. MS FEB exact mass calculated for C$_{29}$H$_{23}$N$_4$O$_4$: m/z=479.1845. Found: 479.1845.

Preparation of Example 13

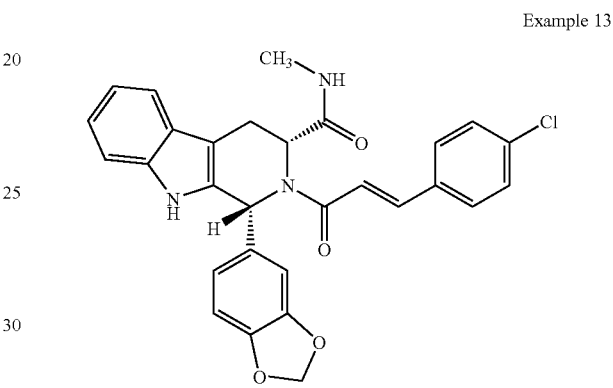

Example 13

Example 13 was prepared in an identical manner to Example 12 and substituting p-chloro trans cinnamic acid for trans cinnamic acid.

$^1$H NMR (DMSO-d$_6$) δ: 2.18 (br s, 1.5H), 2.35 (br S, 1H), 2.50 (m, 1H), 2.51 (br s, 2H), 2.73 (br s, 1H), 2.77 (dd, J=5.8 Hz, 15 Hz, 1H), 3.24–3.40 (m, 0.5H), 5.75 (br s, 1H), 5.95 (s, 2H), 6.68 (br s, 1H), 6.78–7.10 (m, 5H), 7.26–7.37 (m, 1H), 7.46–7.50 (m, 7H), 10.75 (br s, 0.5H), 10.88 (br s, 0.5H); MS ES+m/e 528.2 (p+1), MS ES–m/e 526.2 (p-1).

The following intermediates have been prepared, and can be used to provide a composition of structural formula (I) by the methods set forth above. In particular, an intermediate is reacted with a carboxylic acid, or a carboxylic acid derivative, having the desired (X)$_n$—Y residue. As demonstrated hereafter, the following intermediates also are potent and selective inhibitors of PDE5, and, like compounds of structural formula (I), can be used in a variety of therapeutic areas wherein such inhibition is considered beneficial.

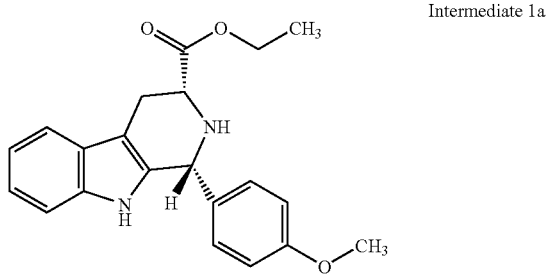

Intermediate 1a

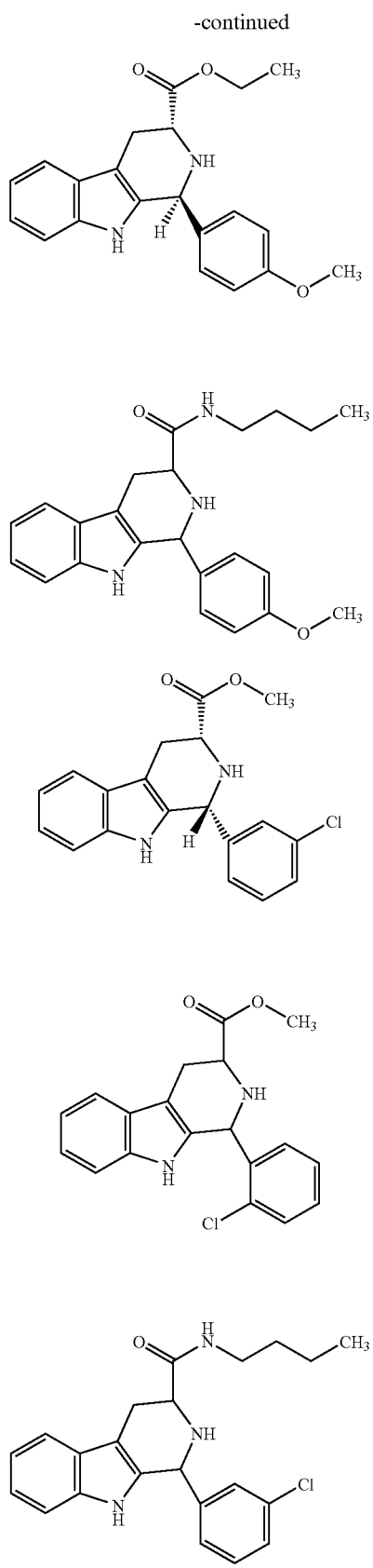

-continued
Intermediate 9b
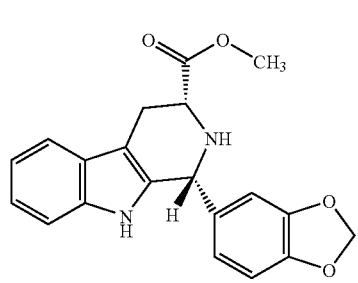
Intermediate 10
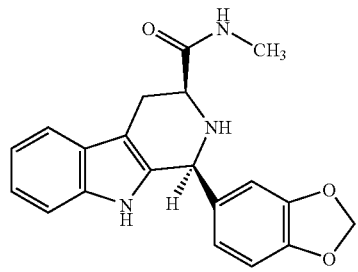
Intermediate 11
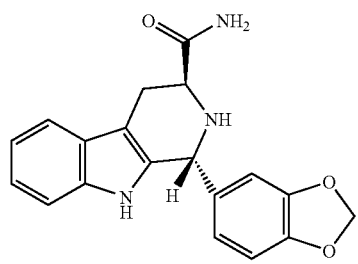
Intermediate 12
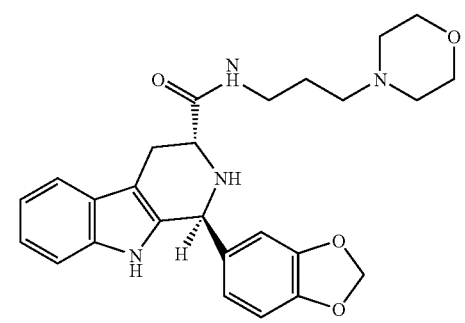
Intermediate 13a
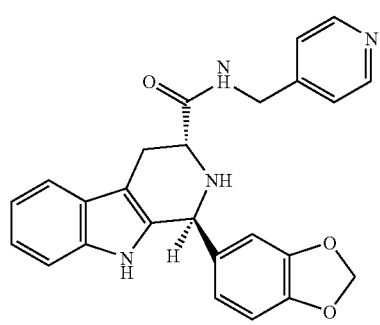
-continued
Intermediate 13b
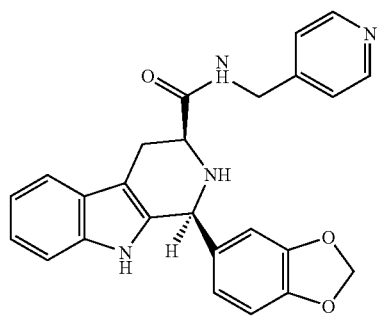
Intermediate 14
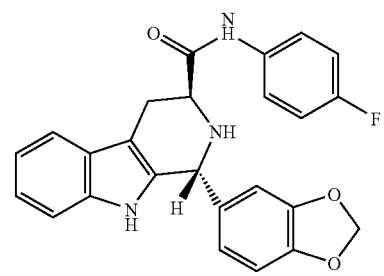
Intermediate 15a
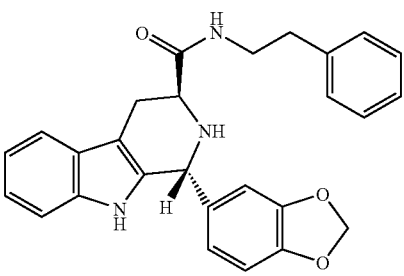
Intermediate 15b
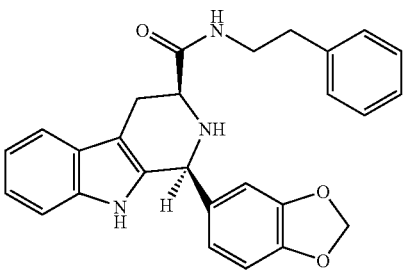
Intermediate 16a -continued
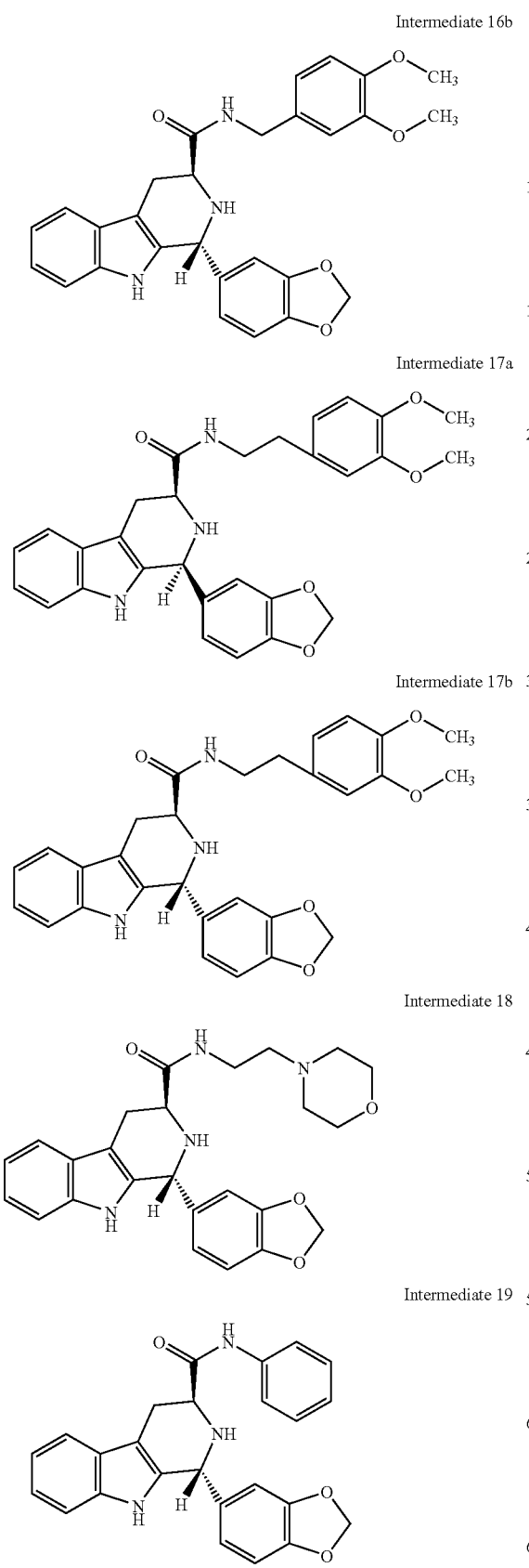
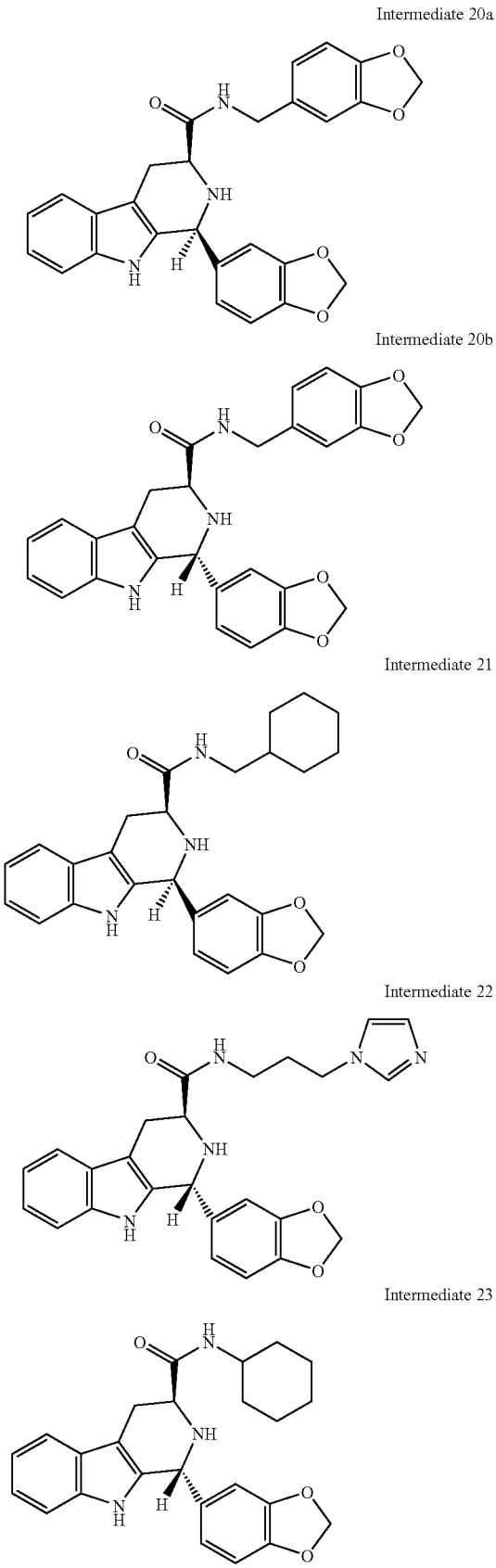

Intermediate 24a
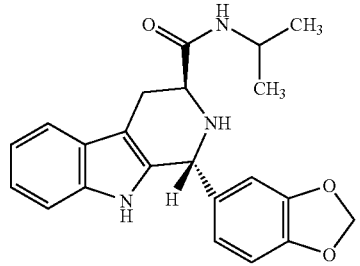
Intermediate 24b
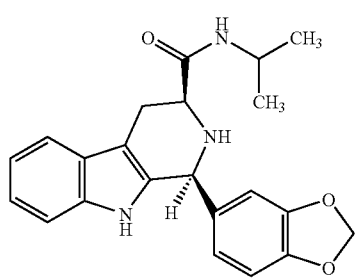
Intermediate 25
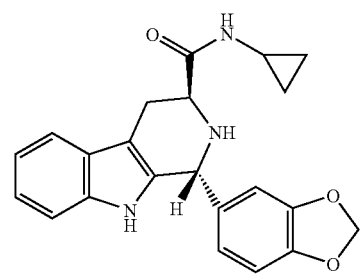
Intermediate 26a
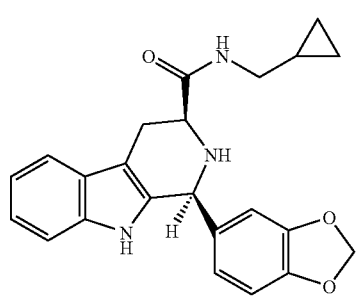
Intermediate 26b
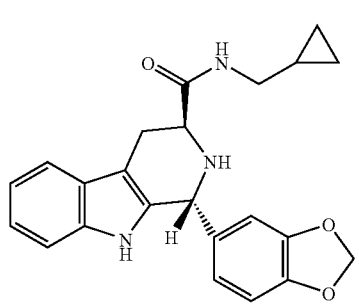
Intermediate 27
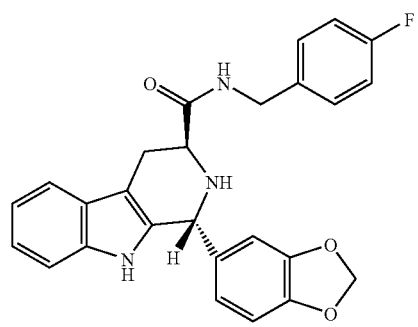
Intermediate 28
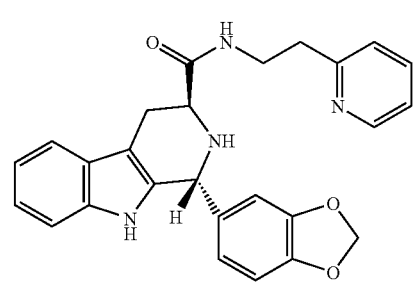
Intermediate 29a
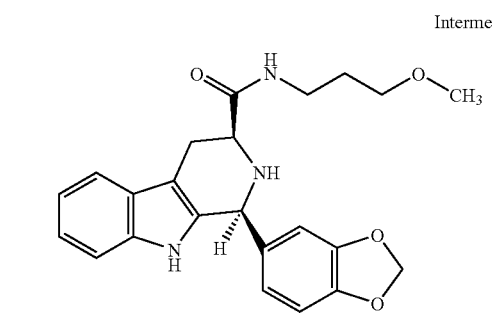
Intermediate 29b
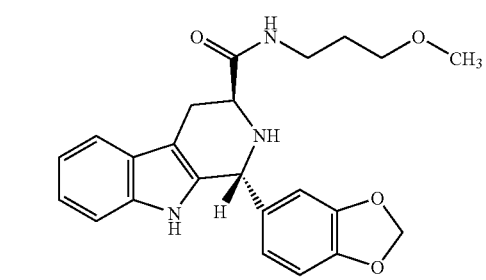
Intermediate 30a
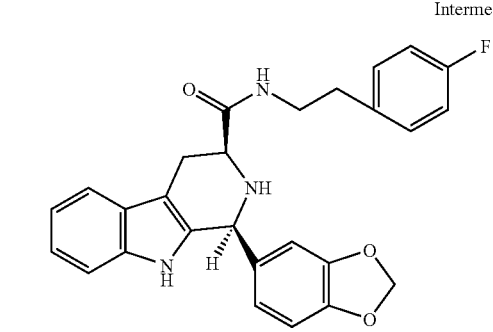

Intermediate 30b
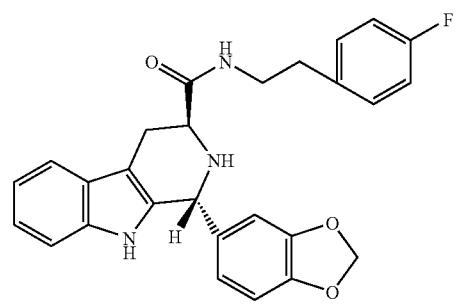
Intermediate 31
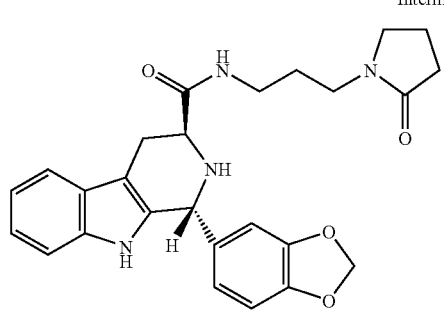
Intermediate 32
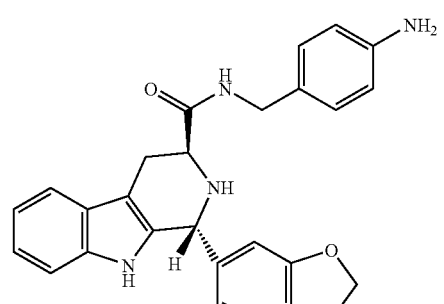
Intermediate 33
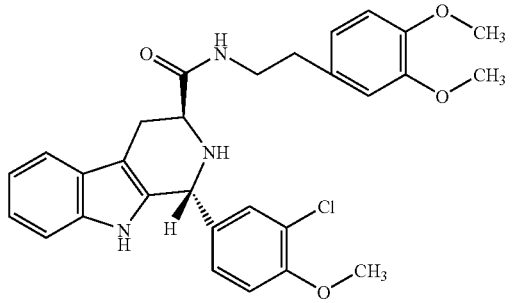
Intermediate 34
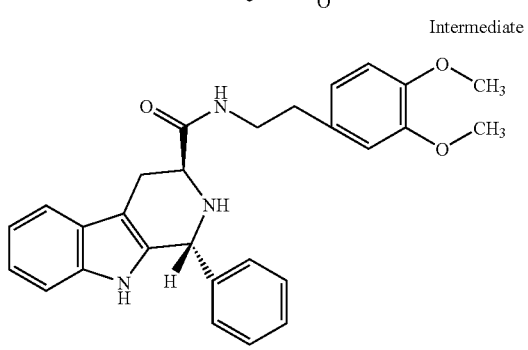
Intermediate 35
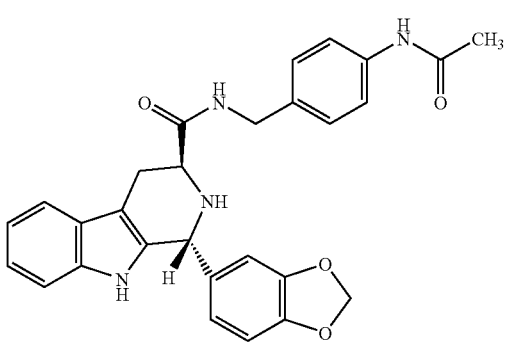
Intermediate 36
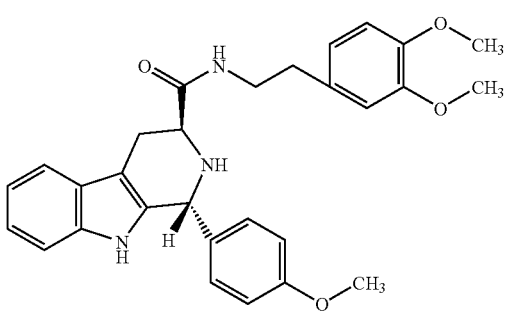
Intermediate 37
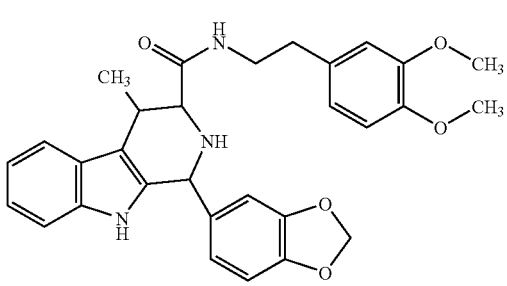
Intermediate 38
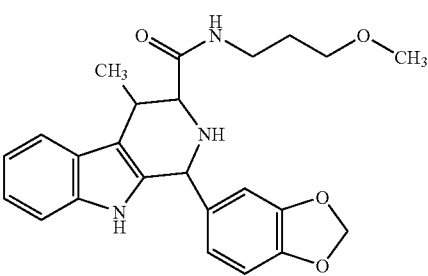
Intermediate 39
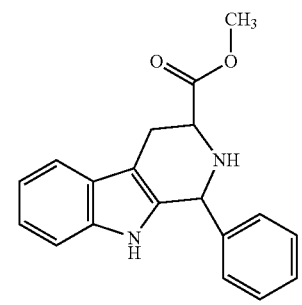

Compounds of the present invention can be formulated into tablets for oral administration. For example, a compound of formula (I) can be formed into a dispersion with a polymeric carrier by the coprecipitation method set forth in WO 96/38131, incorporated herein by reference. The coprecipitated dispersion then can be blended with excipients, then pressed into tablets, which optionally are film-coated.

The compounds of structural formula (I) were tested for an ability to inhibit PDE5. The ability of a compound to inhibit PDE5 activity is related to the $IC_{50}$ value for the compound, i.e., the concentration of inhibitor required for 50% inhibition of enzyme activity. The $IC_{50}$ value for compounds of structural formula (I) were determined using recombinant human PDE5.

The compounds of the present invention typically exhibit an $IC_{50}$ value against recombinant human PDE5 of less than about 50 μM, and preferably less than about 25 μM, and more preferably less than about 15 μm. The compounds of the present invention typically exhibit an $IC_{50}$ value against recombinant human PDE5 of less than about 1 μM, and often less than about 0.5 μM. To achieve the full advantage of the present invention, a present PDE5 inhibitor has an $IC_{50}$ of about 0.1 nM to about 15 μM.

The production of recombinant human PDEs and the $IC_{50}$ determinations can be accomplished by well-known methods in the art. Exemplary methods are described as follows:

EXPRESSION OF HUMAN PDEs

Expression in *Saccharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the *Saccharomyces cerevisiae* host was the protease-deficient strain BJ2-54 deposited on Aug. 31, 1998 with the American Type Culture Collection, Manassas, Virginia, under accession number ATCC 74465. Transformed host cells were grown in 2×SC-leu medium, pH 6.2, with trace metals, and vitamins. After 24 hours, YEP medium-containing glycerol was added to a final concentration of 2×YET/3% glycerol. Approximately 24 hr later, cells were harvested, washed, and stored at −70° C.

HUMAN PHOSPHODIESTERASE PREPARATIONS

Phosphodiesterase Activity Determinations

Phosphodiesterase activity of the preparations was determined as follows. PDE assays utilizing a charcoal separation technique were performed essentially as described in Loughney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 μL reaction mixture containing (final concentrations) 40 mM Tris HCl (pH 8.0), 1 μM $ZnSO_4$, 5 mM $MgCl_2$, and 0.1 mg/mL bovine serum albumin (BSA). PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) μg of Crotalus atrox venom then was added, and the incubation was continued for 3 minutes (15 minutes. total). The reaction was stopped by addition of 200 μL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Purification of PDE5 from *S. cerevisiae*

Cell pellets (29 g) were thawed on ice with an equal volume of Lysis Buffer (25 mM Tris HCl, pH 8, 5 mM $MgCl_2$, 0.25 mM DTT, 1 mM benzamidine, and 10 μM $ZnSO_4$). Cells were lysed in a Microfluidizer® (Microfluidics Corp.) using nitrogen at 20,000 psi. The lysate was centrifuged and filtered through 0.45 μm disposable filters. The filtrate was applied to a 150 mL column of Q SEPHAROSE® FastFlow (Pharmacia). The column was washed with 1.5 volumes of Buffer A (20 mM Bis-Tris Propane, pH 6.8, 1 mM $MgCl_2$, 0.25 mM DTT, 10 μM $ZnSO_4$) and eluted with a step gradient of 125 mM NaCl in Buffer A followed by a linear gradient of 125–1000 mM NaCl in Buffer A. Active fractions from the linear gradient were applied to a 180 mL hydroxyapatite column in Buffer B (20 mM Bis-Tris Propane (pH 6.8), 1 mM $MgCl_2$, 0.25 mM DTT, 10 μM $ZnSO_4$, and 250 mM KCl). After loading, the column was washed with 2 volumes of Buffer B and eluted with a linear gradient of 0–125 mM potassium phosphate in Buffer B. Active fractions were pooled, precipitated with 60% ammonium sulfate, and resuspended in Buffer C (20 mM Bis-Tris Propane, pH 6.8, 125 mM NaCl, 0.5 mM DTT, and 10 μM $ZnSO_4$). The pool was applied to a 140 mL column of SEPHACRYL® S-300 HR and eluted with Buffer C. Active fractions were diluted to 50% glycerol and stored at −20° C.

The resultant preparations were about 85% pure by SDS-PAGE. These preparations had specific activities of about 3 μmol cGMP hydrolyzed per minute per milligram protein.

Inhibitory Effect on cGMP-PDE cGMP-PDE activity of compounds of the present invention was measured using a one-step assay adapted from Wells et al., *Biochim. Biophys. Acta*, 384, 430 (1975). The reaction medium contained 50 mM Tris-HCl, pH 7.5, 5 mM magnesium acetate, 250 μg/ml 5'-Nucleotidase, 1 mM EGTA, and 0.15 μM 8-[$H^3$]-cGMP. Unless otherwise indicated, the enzyme used was a human recombinant PDE5 (ICOS Corp., Bothell, Wash.).

Compounds of the invention were dissolved in DMSO finally present at 2% in the assay. The incubation time was 30 minutes during which the total substrate conversion did not exceed 30%.

The $IC_{50}$ values for the compounds examined were determined from concentration-response curves typically using concentrations ranging from 10 nM to 10 μM. Tests against other PDE enzymes using standard methodology showed that compounds of the invention are selective for the cGMP-specific PDE enzyme.

Biolocical Data

The compounds according to the present invention were typically found to exhibit an $IC_{50}$ value of less than 500 nM (i.e., 0.5 μM). In vitro test data for representative compounds of the invention is given in the following table:

TABLE 1

| In vitro Results (Examples) | |
|---|---|
| Example | PDE5 IC$_{50}$ (µM) |
| 1 | 0.044 |
| 3 | 0.241 |
| 4[1)] | 0.2 |
| 5[1)] | 0.49 |
| 6 | 0.23 |
| 7[1)] | 1 |
| 8 | .502 |
| 9 | .261 |
| 11 | .629 |
| 12 | .03 |
| 13 | .42 |

[1)]vs. bovine aorta

The intermediates also exhibited a low IC$_{50}$ value of less than 900 nM, typically less than 1 µM (i.e., 1000 nM), and often less than 0.5 µM, as illustrated in the following summary of in vitro test data.

TABLE 2

| In vitro Results (Intermediates) | |
|---|---|
| Intermediate | PDE5 IC$_{50}$ (µM) |
| 1a[1)] | 0.85 |
| 1b[1)] | 0.65 |
| 2[1)] | 0.2 |
| 3[1)] | 0.5 |
| 4[1)] | 0.8 |
| 5[1)] | 0.9 |
| 6 | 0.51 |
| 7a[1)] | 0.2 |
| 7b[1)] | 0.7 |
| 8 | 0.76 |
| 9a[1)] | 0.47 |
| 9b | 0.36 |
| 10 | 0.86 |
| 11 | 0.89 |
| 12 | 0.96 |
| 13a | 0.27 |
| 13b | 0.3 |
| 14 | 0.48 |
| 15a | 0.29 |
| 15b | 0.92 |
| 16a | 0.53 |
| 16b | 0.31 |
| 17a | 0.38 |
| 17b | 0.12 |
| 18 | 0.42 |
| 19 | 0.36 |
| 20a | 0.65 |
| 20b | 0.34 |
| 21 | 0.68 |
| 22 | 0.68 |
| 23 | 0.8 |
| 24a | 0.94 |
| 24b | 0.92 |
| 25 | 0.59 |
| 26a | 0.82 |
| 26b | 0.54 |
| 27 | 0.83 |
| 28 | 0.22 |
| 29a | 0.34 |
| 29b | 0.23 |
| 30a | 0.78 |
| 30b | 0.42 |
| 31 | 0.43 |
| 32 | 0.33 |
| 33 | 0.86 |
| 34 | 0.23 |
| 35 | 0.16 |
| 36 | 0.09 |
| 37 | 0.62 |
| 38 | 0.77 |
| 39 | 0.65 |

[1)]vs. bovine aorta

Obviously, many modifications and variations of the invention as hereinbefore set forth can be made without departing from the spirit and scope thereof, and, therefore, only such limitations should be imposed as are indicated by the appended claims.

What is claimed is:

1. A compound having a formula

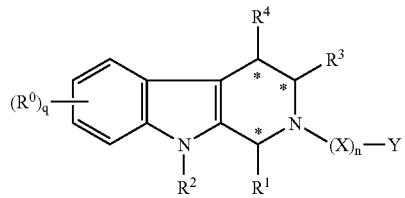

wherein R$^0$, independently, is selected from the group consisting of halo, C$_{1-6}$alkyl, aryl, heteroaryl, C$_{3-8}$cycloalkyl, C$_{3-8}$heterocycloalkyl, C$_{3-8}$cycloalkylQ, C(=O)R$^a$, OC(=O)R$^a$, C(=O)OR$^a$, C$_{1-4}$alkyleneNR$^a$R$^b$, C$_{1-4}$alkyleneHet, C$_{1-4}$alkyleneC(=O)OR$^a$, C(=O)NR$^a$SO$_2$R$^c$, C(=O)C$_{1-4}$alkyleneHet, C(=O)NR$^a$R$^b$, C(=O)NR$^a$R$^c$, C(=O)NR$^a$C$_{1-4}$alkyleneoR$^b$, C(=O)NR$^a$C$_{1-4}$alkyleneHet, OR$^a$, OC$_{1-4}$alkyleneC(=O)OR$^a$, OC$_{1-4}$alkyleneNR$^a$R$^b$, OC$_{1-4}$alkyleneHet, OC$_{1-4}$alkyleneOR$^a$, OC$_{1-4}$alkyleneNR$^a$C(=O)OR$^b$, NR$^a$R$^b$, NR$^a$C$_{1-4}$alkyleneNR$^a$R$^b$, NR$^a$C(=O)R$^b$, NR$^a$C(=O)NR$^a$R$^b$, N(SO$_2$C$_{1-4}$alkyl)$_2$, NR$^a$(SO$_2$C$_{1-4}$alkyl), nitro, trifluoromethyl, trifluoromethoxy, cyano, SO$_2$NR$^a$R$^b$, SO$_2$R$^a$, SOR$^a$, SR$^a$, and OSO$_2$CF$_3$;

R$^1$ is selected from the group consisting of aryl optionally substituted with one or both of alkoxy and halo, an optionally substituted C$_{3-8}$cycloalkyl ring, an optionally substituted C$_{3-8}$heterocycloalkyl ring, an optionally substituted bicyclic ring

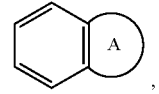

wherein the fused ring A is a 5- or 6-membered ring, saturated or partially or fully unsaturated, and contains carbon atoms and optionally one to three heteroatoms selected from oxygen, sulfur, and nitrogen, hydrogen, C$_{1-6}$alkyl, arylC$_{1-3}$alkyl, C$_{1-3}$alkylenearyl, haloC$_{1-6}$alkyl, C$_{1-4}$alkyleneC(=O)OR$^a$, C$_{1-4}$alkyleneC(=O)NR$^a$R$^b$, C$_{3-8}$cycloalkyl, C$_{3-8}$cycloalkenyl, C$_{3-8}$heterocycloalkenyl, C$_{1-4}$alkyleneHet, C$_{1-4}$alkyleneQR$^a$, C$_{2-6}$alkenyleneQR$^a$, C$_{1-4}$alkyleneQC$_{1-4}$alkyleneQR$^a$, and a spiro substituent having a structure R² is selected from the group of hydrogen, C₁₋₆alkyl, C₃₋₈cycloalkyl, C₃₋₈heterocycloalkyl, C₂₋₆alkenyl, C₁₋₃alkylenearyl, arylC₁₋₃alkyl, C(=O)Rᵃ, aryl, heteroaryl, C(=O)Rᵃ, C(=O)NRᵃRᵇ, C(=O)NRᵃRᶜ, C(=S)NRᵃRᵇ, C(=S)NRᵃRᶜ, SO₂Rᵃ, SO₂NRᵃRᵇ, S(=O)Rᵃ, S(=O)NRᵃRᵇ, C(=O)NRᵃC₁₋₄alkyleneORᵃ, C(=O)NRᶜC₁₋₄alkyleneHet, C(=O)C₁₋₄alkylenearyl, C(=O)C₁₋₄alkyleneheteroaryl, C₁₋₄alkylenearyl substituted with one or more of SO₂NRᵃRᵇ, NRᵃRᵇ, C(=O)ORᵃ, NRᵃSO₂CF₃, CN, NO₂, C(=O)Rᵃ, ORᵃ, C₁₋₄alkyleneNRᵃRᵇ, and OC₁₋₄alkyleneNRᵃRᵇ, C₁₋₄alkyleneheteroaryl, C₁₋₄alkyleneHet, C₁₋₄alkyleneC(=O)C₁₋₄alkylenearyl, C₁₋₄alkyleneC(=O)C₁₋₄alkyleneheteroaryl, C₁₋₄alkyleneC(=O)Het, C₁₋₄alkyleneC(=O)NRᵃRᵇ, C₁₋₄alkyleneORᵃ, C₁₋₄alkyleneNRᵃC(=O)Rᵃ, C₁₋₄alkyleneoC₁₋₄alkyleneORᵃ, C₁₋₄alkyleneNRᵃRᵇ, C₁₋₄alkyleneC(=O)ORᵃ, and C₁₋₄alkyleneaC₁₋₄alkyleneC(=O)ORᵃ;

R³ is selected from the group consisting of C(=O)Rᵇ, C(=O)ORᵇ, C(=O)NRᵃRᵇ, C(=O)NRᵃRᶜ, C(=S)NRᵃRᵇ, C(=S)NRᵃRᶜ, C(=O)Het, C(=O)NRᵃC₁₋₄alkyleneORᵃ, C(=O)NRᵃC₁₋₄alkyleneHet, C(=O)C₁₋₄alkylenearyl, C(=O)C₁₋₄alkyleneheteroaryl, C(=O)NRᵃC₁₋₄alkylenearyl, C(=O)NRᵃC₁₋₄alkyleneC₃₋₈cycloalkyl, C(=O)NRᵇSO₂Rᶜ, C(=O)NRᵃC₁₋₄alkyleneOC₁₋₆alkyl, C(=O)NRᵃC₁₋₄alkyleneheteroaryl, NRᵃRᶜ, NRᵃC(=O)Rᵇ, NRᵃC(=O)NRᵃRᶜ, NRᵃ(SO₂C₁₋₄alkyl), N(SO₂C₁₋₄alkyl)₂, ORᵃ, NRᵃC(=O)C₁₋₄alkyleneN(Rᵇ)₂, NRᵃC(=O)C₁₋₄alkyleneC(=O)ORᵃ, NRᵃ(C=O)C₁₋₃alkylenearyl, NRᵃC(=O)C₁₋₃alkyleneC₃₋₈heterocycloalkyl, NRᵃC(=O)C₁₋₃alkyleneHet, and C(=O)NRᵃSO₂Rᵇ;

R⁴ is selected from the group consisting of hydrogen, C₁₋₆alkyl, aryl, heteroaryl, arylC₁₋₃alkyl, C₁₋₃alkylenearyl, C₁₋₃alkyleneHet, C₃₋₈cycloalkyl, and C₃₋₈heterocycloalkyl;

X is selected from the group consisting of C(=O), (CH₂)ₜC(=O), C(=O)C≡C, C(=S), SO, SO₂, SO₂C(Rᵃ)=CRᵃ, CRᵃ=CRᵃ, C(=O)NRᵃ, and C(=N—ORᵃ);

Y is Rᵃ;

Rᵃ is selected from the group consisting of hydrogen, C₁₋₆alkyl, C₃₋₆cycloalkyl, phenyl, phenylC₁₋₃alkyl, and C₁₋₃alkylenephenyl;

Rᵇ is selected from the group consisting of hydrogen, C₁₋₆alkyl, C₃₋₈cycloalkyl, C₁₋₃alkyleneN(Rᵃ)₂, aryl, arylC₁₋₃alkyl, C₁₋₃alkylenearyl, and heteroaryl;

Rᶜ is selected from the group consisting of hydrogen, C₁₋₆alkyl, aryl, heteroaryl, arylC₁₋₃alkyl, heteroarylC₁₋₃alkyl, C₁₋₃alkyleneN(Rᵃ)2, C₁₋₆alkylenearyl, C₁₋₆alkyleneHet, haloC₁₋₆alkyl, C₃₋₈cycloalkyl, C₃₋₈heterocycloalkyl, Het, C₁₋₃alkyleneheteroaryl, C₁₋₆alkyleneC(=O)ORᵃ, and C₁₋₃alkyleneC₃₋₈heterocycloalkyl;

or Rᵃ and Rᶜ are taken together to form a 5- or 6-membered ring, optionally containing at least one heteroatom;

Q is O, S, or NRʰ;

B is O, S, or NRʰ;

C is O, S, or NRᵃ;

D is CRᵃ, or N;

E is CRᵃ, C(Rᵃ)₂, or NRʰ; and

Rʰ is null or is selected from the group consisting of hydrogen, C₁₋₆alkyl, aryl, heteroaryl, arylC₁₋₃alkyl, heteroarylC₁₋₃alkyl, C₁₋₃alkylenearyl, and C₁₋₃alkyleneheteroaryl;

Het represents a 5- or 6-membered heterocyclic ring, saturated or partially or fully unsaturated, containing at least one heteroatom selected from the group consisting of oxygen, nitrogen, and sulfur, and optionally substituted with C₁₋₄alkyl or C(=O)ORᵃ;

n is 1;

q is 0, 1, 2, 3, or 4;

t is 1, 2, 3, or 4;

or a pharmaceutically acceptable salt or solvate thereof.

2. The compound of claim 1 represented by the formula or a pharmaceutically acceptable salt or solvate thereof.

3. The compound of claim 1 wherein q is 0, or R⁰ is selected from the group consisting of aryl, Het, ORᵃ, C(=O)ORᵃ, C₁₋₄alkyleneNRᵃRᵇ, OC(=O)Rᵃ, C(=O)Rᵃ, NRᵃRᵇ, C₃₋₈cycloalkyl, C₃₋₈cycloalkylQ, C(=O)NRᵃRᵇ, and C(=O)NRᵃRᶜ.

4. The compound of claim 1 wherein R¹ is selected from the group consisting of optionally substituted aryl, C₁₋₄alkyleneQRᵃ, C₁₋₄alkyleneQC₁₋₄alkyleneQRᵃ, C₃₋₈cycloalkyl, C₃₋₈cycloalkenyl, C₁₋₆alkyl, -continued

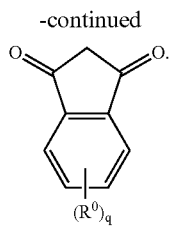

5. The compound of claim 1 wherein $R^1$ is the optionally substituted bicyclic ring system

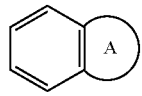

6. The compound of claim 5 wherein $R^1$ is

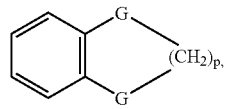

and wherein p is an integer 1 or 2, and G, independently, are $C(R^a)_2$, O, S, or $NR^a$.

7. The compound of claim 1 wherein $R^1$ is selected from the group consisting of

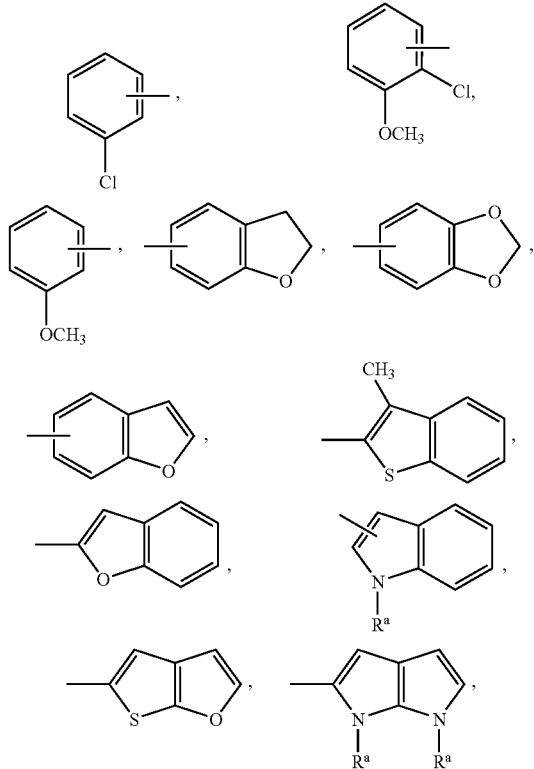

-continued

—CH$_2$OR$^a$, —CH$_2$OCH$_2$OR$^a$, 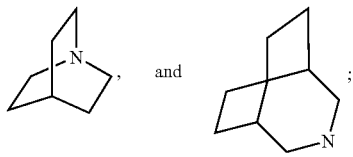 and

8. The compound of claim 1 wherein $R^2$ is selected from the group consisting of hydrogen, aryl, heteroaryl, OR$^a$, NR$^a$R$^b$, NR$^a$R$^c$, C$_{1-4}$alkyleneHet, C$_{1-4}$alkyleneheteroaryl, C$_{1-4}$alkylenearyl, C$_{1-4}$alkyleneC(=O)C$_{1-4}$alkylenearyl, C$_{1-4}$alkyleneC(=O)OR$^a$, C$_{1-4}$alkyleneC(=O)NR$^a$R$^b$, C$_{1-4}$alkyleneC(=O)NR$^a$R$^c$, C$_{1-4}$alkyleneC(=O)Het, C$_{1-4}$alkyleneNR$^a$R$^b$, C$_{1-4}$alkyleneNR$^a$R$^c$, C$_{1-4}$alkyleneNR$^a$C(=O)R$^a$, and C$_{1-4}$alkyleneOC$_{1-4}$alkyleneOR$^a$.

9. The compound of claim 8 wherein $R^2$ is selected from the group consisting of hydrogen; C$_{1-4}$alkyleneheteroaryl, wherein the heteroaryl group is selected from the group consisting of benzimidazole, a triazole, and imidazole; C$_{1-4}$alkyleneHet, wherein Het is selected from the group consisting of piperazine, morpholine, pyrrolidine, pyrrolidone, tetrahydrofuran, piperidine,

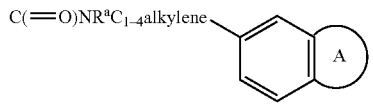

C$_{1-4}$alkyleneC$_6$H$_5$, optionally substituted with one to three groups selected from the group consisting of C(=O)OR$^a$, NR$^a$R$^b$, NR$^a$SO$_2$CF$^3$, SO$_2$NR$^a$R$^b$, CN, OR$^a$, C(=O)R$^a$, C$_{1-4}$alkyleneNR$^a$R$^b$, nitro, OC$_{1-4}$alkylenearyl, and OC$_{1-4}$alkyleneNR$^a$R$^b$; C$_{1-4}$alkyleneC(=O)benzyl; C$_{1-4}$alkyleneC(=O)OR$^a$; C$_{1-4}$alkyleneC(=O)NR$^a$R$^b$; C$_{1-4}$alkyleneC(=O)NR$^a$R$^c$; C$_{1-4}$alkyleneHet; NR$^a$R$^b$; OH; OC$_{1-4}$alkyl; C$_6$H$_5$; C$_{1-4}$alkyleneNR$^a$R$^b$; C$_{1-4}$alkyleneOR$^a$; C$_{1-4}$alkyleneNHC(=O)R$^a$; and C$_{1-4}$alkyleneOC$_{1-4}$alkyleneOR$^a$.

10. The compound of claim 8 wherein $R^2$ is selected from the group consisting of C$_{1-6}$alkyl, C(=O)OR$^a$, C(=O)R$^a$, hydrogen, C(=O)NR$^a$C$_{1-4}$alkyleneHet, C(=O)NR$^a$R$^c$, aryl, and heteroaryl.

11. The compound of claim 1 wherein $R^3$ is selected from the group consisting of C(=O)OR$^b$, C(=O)R$^b$, C(=O)NR$^a$C$_{1-4}$alkyleneOC$_{1-6}$alkyl, C(=O)NR$^a$C$_{1-4}$alkyleneC$_{3-8}$cycloalkyl, C(=O)Het, C(=O)NR$^a$C$_{1-4}$alkylene—[ring A]

C(=O)NR$^a$C$_{1-4}$alkyleneheteroaryl, C(=O)NR$^a$C$_{1-4}$alkylenearyl, C(=O)NR$^a$C$_{1-4}$alkyleneHet, C(=O)NR$^a$R$^c$, and C(=S)NR$^a$R$^c$.

12. The compound of claim 1 wherein $R^4$ is selected from the group consisting of hydrogen, $C_{1-6}$alkyl, aryl, and heteroaryl.

13. The compound of claim 1 wherein X is selected from the group consisting of C(=O), $(CH_2)_rC=O$, C(=S) and C(=N—$OR^a$).

14. The compound of claim 1 wherein q is 0, or $R^0$ is selected from the group consisting of halo, methyl, trifluoromethyl, and trifluoromethyl; $R^1$ is selected from the group consisting of

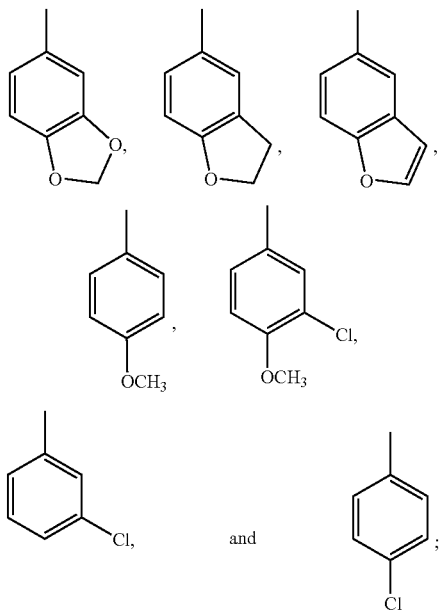

$R^2$ is selected from the group consisting of hydrogen, $C_{1-6}$alkyl, C(=O)$NR^aR^c$, and $C_{1-4}$alkyleneHet; $R^3$ is selected from the group consisting of C(=O)$OC_2H_5$, C(=O)$OCH_3$, C(=O)$NHCH_2C_6H_5$, C(=O)$NH(CH_2)_2$ $C_6H_5$, C(=O)$NHC_6H_5$, C(=O)$NH_2$, C(=O)$N(CH3)_2$, C(=S)$N(CH_3)_2$, C(=O)$NH(CH_2)_2CH_3$, C(=O)$N(CH_2)_3$ $CH_3$, C(=O)$NHCH_3$, C(=O)$NHCH(CH_3)_2$, C(=O)NH $(CH_2)_3OCH_3$,

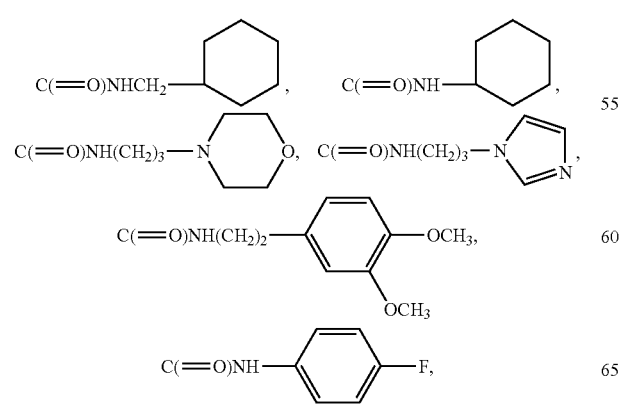

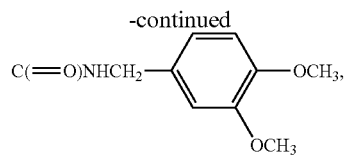

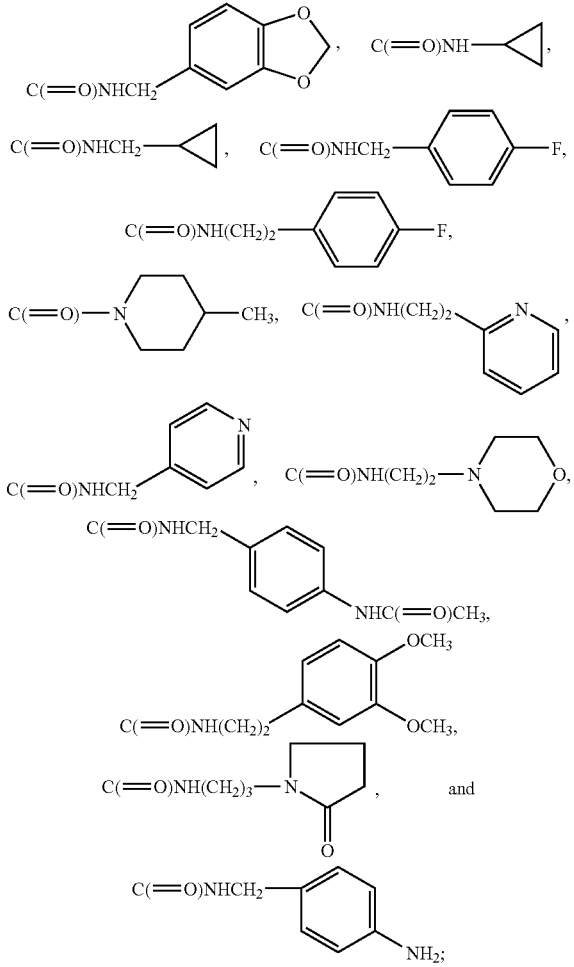

and $R^4$ is hydrogen or $C_{1-6}$alkyl.

15. The compound of claim 1 wherein q is 0, $R^2$ is hydrogen, and $R^4$ is hydrogen or methyl.

16. A compound selected from the group consisting of

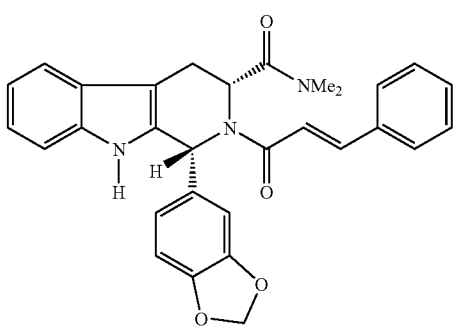

53
-continued
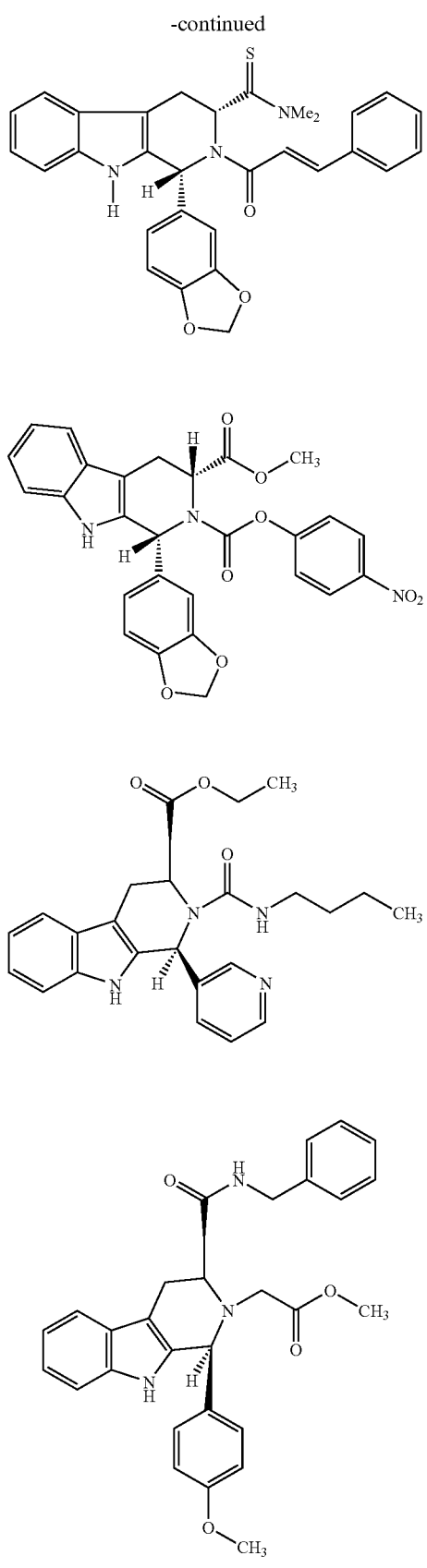
54
-continued
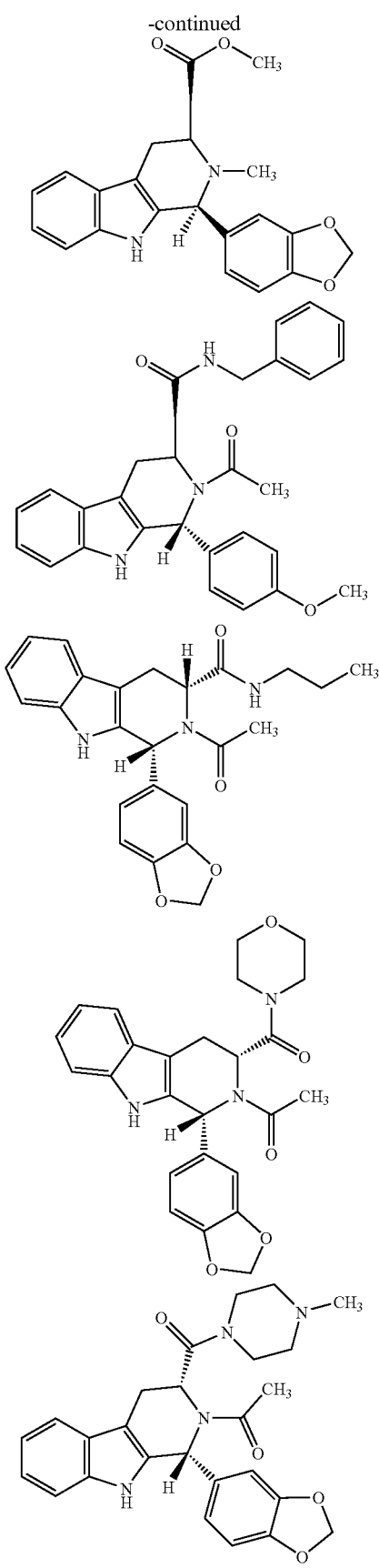

-continued

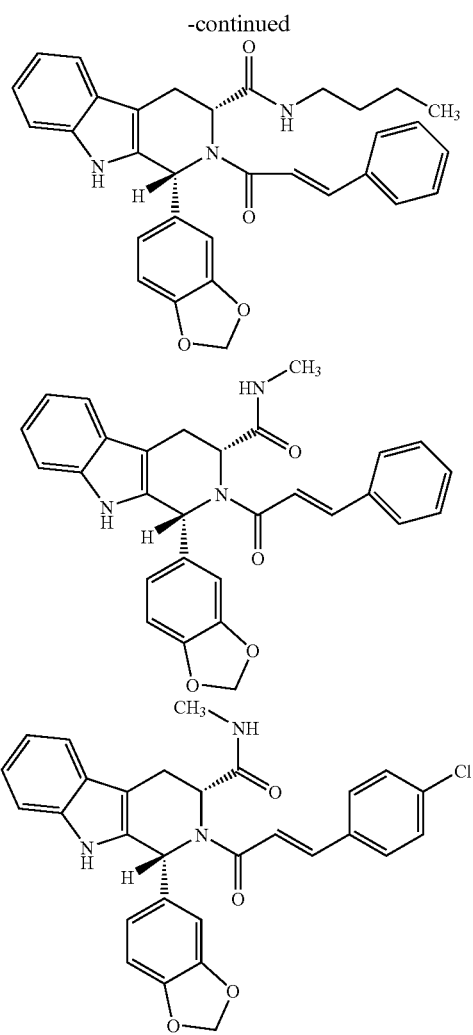

or a pharmaceutically acceptable salt or solvate thereof.

17. A pharmaceutical composition comprising a compound of claim 1, together with a pharmaceutically acceptable diluent or carrier.

18. A method of treating a male animal for male erectile dysfunction comprising administering to said male animal an effective amount of a pharmaceutical composition comprising a compound of claim 1, together with a pharmaceutically acceptable diluent or carrier.

19. The method of claim 18 wherein the treatment is an oral treatment.

20. A method for the prophylactic treatment of male erectile dysfunction comprising administration of an effective dose of a compound of claim 1, or a pharmaceutically acceptable salt or solvate thereof, to a male animal.

21. A compound having a formula

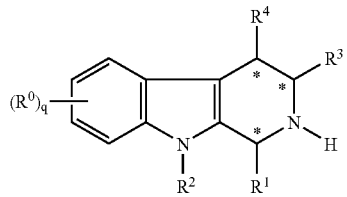

wherein $R^0$, independently, is selected from the group consisting of halo, $C_{1-6}$alkyl, aryl, heteroaryl, $C_{3-8}$cycloalkyl, $C_{3-8}$heterocycloalkyl, $C_{3-8}$cycloalkylQ, $C(=O)R^a$, $OC(=O)R^a$, $C(=O)OR^a$, $C_{1-4}$alkyleneN-$R^aR^b$, $C_{1-4}$alkyleneHet, $C_{1-4}$alkyleneC(=O)OR$^a$, $C(=O)NR^aSO_2R^c$, $C(=O)C_{1-4}$alkyleneHet, $C(=O)NR^aR^b$, $C(=O)NR^aR^c$, $C(=O)NR^aC_{1-4}$alkyleneOR$^b$, $C(=O)NR^aC_{1-4}$alkyleneHet, $OR^a$, $OC_{1-4}$alkyleneC(=O)OR$^a$, $OC_{1-4}$alkyleneNR$^aR^b$, $OC_{1-4}$alkyleneHet, $OC_{1-4}$alkyleneOR$^a$, $OC_{1-4}$alkyleneNR$^aC(=O)OR^b$, $NR^aR^b$, $NR^aC_{1-4}$alkyleneNR$^aR^b$, $NR^aC(=O)R^b$, $NR^aC(=O)NR^aR^b$, $N(SO_2C_{1-4}$alkyl$)_2$, $NR^a(SO_2C_{1-4}$alkyl), nitro, trifluoromethyl, trifluoromethoxy, cyano, $SO_2NR^aR^b$, $SO_2R^a$, $SOR^a$, $SR^a$, and $OSO_2CF_3$;

$R^1$ is selected from the group consisting of aryl substituted with one or both of halo and methoxy, optionally substituted heteroaryl, an optionally substituted $C_{3-8}$cycloalkyl ring, an optionally substituted $C_{3-8}$heterocycloalkyl ring, an optionally substituted bicyclic ring

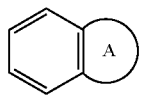

wherein the fused ring A is a 5- or 6-membered ring, saturated or partially or fully unsaturated, and contains carbon atoms and optionally one to three heteroatoms selected from oxygen, sulfur, and nitrogen, $C_{1-4}$alkyleneC(=O)OR$^a$, $C_{1-4}$alkyleneC(=O)NR$^aR^b$, $C_{3-8}$cycloalkyl, $C_{3-8}$cycloalkenyl, $C_{3-8}$heterocycloalkenyl, $C_{1-4}$alkyleneHet, $C_{1-4}$alkyleneQR$^a$, $C_{2-6}$alkenyleneQR$^a$, $C_{1-4}$alkyleneQC$_{1-4}$alkyleneQR$^a$,

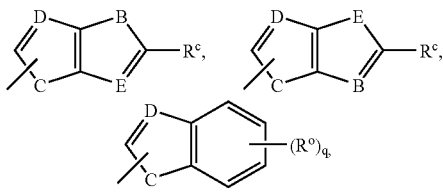

and a spiro substituent having a structure

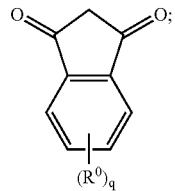

$R^2$ is selected from the group consisting of hydrogen, $C_{1-6}$alkyl, $C_{3-8}$cycloalkyl, $C_{3-8}$heterocycloalkyl, $C_{2-6}$alkenyl, $C_{1-3}$alkylenearyl, aryl$C_{1-3}$alkyl, $C(=O)R^a$, aryl, heteroaryl, $C(=O)R^a$, $C(=O)NR^aR^b$, $C(=O)NR^aR^c$, $C(=S)NR^aR^b$, $C(=S)NR^aR^c$, $SO_2R^a$, $SO_2NR^aR^b$, $S(=O)R^a$, $S(=O)NR^aR^b$, $C(=O)NR^aC_{1-4}$ alkyleneOR$^a$, $C(=O)NR^aC_{1-4}$alkyleneHet, $C(=O)C_{1-4}$alkylenearyl, $C(=O)C_{1-4}$alkyleneheteroaryl, $C_{1-4}$alkylenearyl substituted with one or more of $SO_2NR^aR^b$, $NR^aR^b$, $C(=O)OR^a$, $NR^aSO_2CF_3$, CN, $NO_2$, $C(=O)R^a$, $OR^a$, $C_{1-4}$alkyleneNR$^aR^b$, and $OC_{1-4}$alkyleneNR$^aR^b$, $C_{1-4}$alkyleneheteroaryl, $C_{1-4}$alkyleneHet, $C_{1-4}$alkyleneC(=O)C$_{1-4}$alkylenearyl, $C_{1-4}$alkyleneC(=O)C$_{1-4}$alkyleneheteroaryl, $C_{1-4}$alkyleneC (=O)Het, C<sub>1-4</sub>alkyleneC(=O)NR<sup>a</sup>R<sup>b</sup>, C<sub>1-4</sub>alkyleneOR<sup>a</sup>, C<sub>1-4</sub>alkyleneNR<sup>a</sup>C(=O)R<sup>a</sup>, C<sub>1-4</sub>alkyleneOC<sub>1-4</sub>alkyleneOR<sup>a</sup>, C<sub>1-4</sub>alkyleneNR<sup>a</sup>R<sup>b</sup>, C<sub>1-4</sub>alkyleneC(=O)OR<sup>a</sup>, and C<sub>1-4</sub>alkyleneOC<sub>1-4</sub>alkyleneC(=O)OR<sup>a</sup>;

$R^3$ is selected from the group consisting of $C(=O)R^b$, $C(=O)NR^aR^b$, $C(=O)NR^aR^c$, $C(=S)NR^aR^b$, $C(=S)NR^aR^c$, $C(=O)Het$, $C(=O)NR^aC_{1-4}alkyleneOR^a$, $C(=O)NR^aC_{1-4}alkyleneHet$, $C(=O)C_{1-4}alkylenearyl$, $C(=O)C_{1-4}alkyleneheteroaryl$, $C(=O)NR^aC_{1-4}alkylenearyl$, $C(=O)NR^aC_{1-4}alkyleneC_{3-8}cycloalkyl$, $C(=O)NR^bSO_2R^c$, $C(=O)NR^aC_{1-4}alkyleneOC_{1-6}alkyl$, $C(=O)NR^aC_{1-4}alkyleneheteroaryl$, $NR^aR^c$, $NR^aC(=O)R^b$, $NR^aC(=O)NR^aR^c$, $NR^a(SO_2C_{1-4}alkyl)$, $N(SO_2C_{1-4}alkyl)_2$, $OR^a$, $NR^aC(=O)C_{1-4}alkyleneN(R^b)_2$, $NR^aC(=O)C_{1-4}alkyleneC(=O)OR^a$, $NR^a(C=O)C_{1-3}alkylenearyl$, $NR^aC(=O)C_{1-3}alkyleneC_{3-8}heterocycloalkyl$, $NR^aC(=O)C_{1-3}alkyleneHet$, and $C(=O)NR^aSO_2R^b$;

$R^4$ is selected from the group consisting of hydrogen, $C_{1-6}alkyl$, aryl, heteroaryl, $arylC_{1-3}alkyl$, $C_{1-3}alkylenearyl$, $C_{1-3}alkyleneHet$, $C_{3-8}cycloalkyl$, and $C_{3-8}heterocycloalkyl$;

$R^a$ is selected from the group consisting of hydrogen, $C_{1-6}alkyl$, $C_{3-6}cycloalkyl$, aryl, $arylC_{1-3}alkyl$, $C_{1-3}alkylenearyl$, heteroaryl, $heteroarylC_{1-3}alkyl$, and $C_{1-3}alkyleneheteroaryl$;

$R^b$ is selected from the group consisting of hydrogen, $C_{1-6}alkyl$, $C_{3-8}cycloalkyl$, $C_{1-3}alkyleneN(R^a)_2$, aryl, $arylC_{1-3}alkyl$, $C_{1-3}alkylenearyl$, and heteroaryl;

$R^c$ is selected from the group consisting of hydrogen, $C_{1-6}alkyl$, aryl, heteroaryl, $arylC_{1-3}alkyl$, $heteroarylC_{1-3}alkyl$, $C_{1-3}alkyleneN(R^a)_2$, $C_{1-6}alkylenearyl$, $C_{1-6}alkyleneHet$, $haloC_{1-6}alkyl$, $C_{3-8}cycloalkyl$, $C_{3-8}heterocycloalkyl$, Het, $C_{1-3}alkyleneheteroaryl$, $C_{1-6}alkyleneC(=O)OR^a$, and $C_{1-3}alkyleneC_{3-8}heterocycloalkyl$;

or $R^a$ and $R^c$ are taken together to form a 5- or 6-membered ring, optionally containing at least one heteroatom;

Q is O, S, or $NR^h$;

B is O, S, or $NR^h$;

C is O, S, or $NR^a$;

D is $CR^a$ or N;

E is $CR^a$, $C(R^a)2$, or $NR^h$; and $R^h$ is null or is selected from the group consisting of hydrogen, $C_{1-6}alkyl$, aryl, heteroaryl, $arylC_{1-3}alkyl$, $heteroarylC_{1-3}alkyl$, $C_{1-3}alkylenearyl$, and $C_{1-3}alkyleneheteroaryl$;

Het represents a 5- or 6-membered heterocyclic ring, saturated or partially or fully unsaturated, containing at least one heteroatom selected from the group consisting of oxygen, nitrogen, and sulfur, and optionally substituted with $C_{1-4}alkyl$ or $C(=O)OR^a$;

q is 0, 1, 2, 3, or 4;

or a pharmaceutically acceptable salt or solvate thereof.

22. The compound of claim 21 represented by the formula

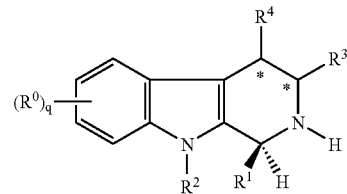

or a pharmaceutically acceptable salt or hydrate thereof.

23. The compound of claim 21 wherein q is 0, or $R^0$ is selected from the group consisting of aryl, Het, $OR^a$, $C(=O)OR^a$, $C_{1-4}alkyleneNR^aR^b$, $OC(=O)R^a$, $C(=O)R^a$, $NR^aR^b$, $C_{3-8}cycloalkyl$, $C_{3-8}cycloalkylQ$, $C(=O)NR^aR^b$, and $C(=O)NR^aR^c$.

24. The compound of claim 21 wherein $R^1$ is selected from the group consisting of aryl substituted with one or both of chloro and methoxy, optionally substituted heteroaryl, $C_{1-4}alkyleneQR^a$, $C_{1-4}alkyleneQC_{1-4}alkyleneQR^a$, $C_{3-8}cycloalkyl$, $C_{3-8}cycloalkenyl$,

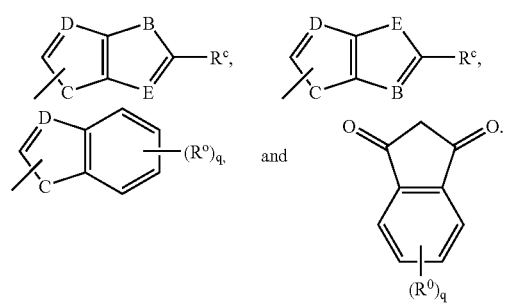

25. The compound of claim 21 wherein $R^1$ is the optionally substituted bicyclic ring system

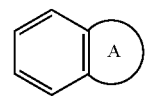

26. The compound of claim 25 wherein $R^1$ is

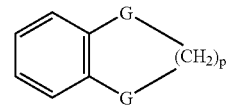

and wherein p is an integer 1 or 2, and G, independently, are $C(R^a)_2$, O, S, or $NR^a$.

27. The compound of claim 21 wherein $R^1$ is selected from the group consisting of

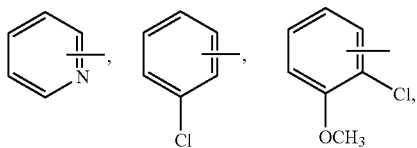

-continued

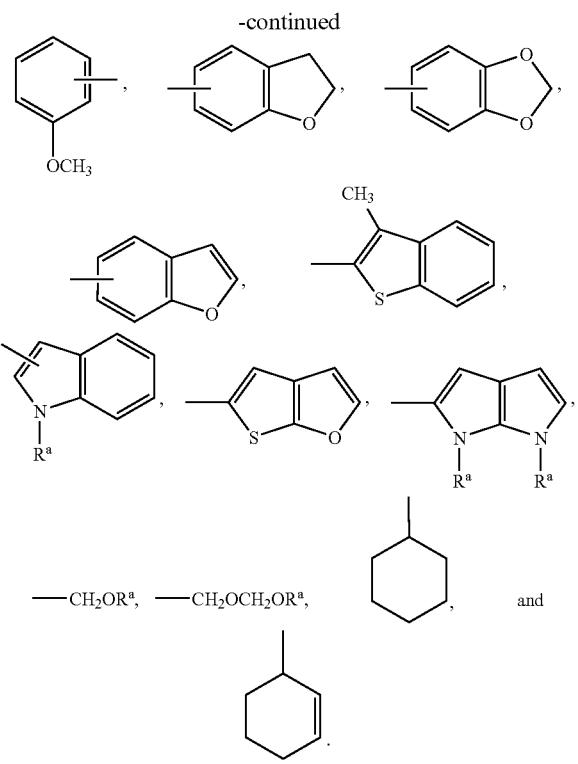

28. The compound of claim 21 wherein $R^2$ is selected from the group consisting of aryl, hydrogen, heteroaryl, $OR^a$, $NR^aR^b$, $NR^aR^c$, $C_{1-4}$alkyleneHet, $C_{1-4}$alkyleneheteroaryl, $C_{1-4}$alkylenearyl, $C_{1-4}$alkyleneC(=O)$C_{1-4}$alkylenearyl, $C_{1-4}$alkyleneC(=O)$OR^a$, $C_{1-4}$alkyleneC(=O)$NR^aR^b$, $C_{1-4}$alkyleneC(=O)$NR^aR^c$, $C_{1-4}$alkyleneC(=O)Het, $C_{1-4}$alkyleneNR^aR^b$, $C_{1-4}$alkyleneNR^aR^c$, $C_{1-4}$alkyleneN-$R^aC(=O)R^a$, and $C_{1-4}$alkyleneOC$_{1-4}$alkyleneOR$^a$.

29. The compound of claim 21 wherein $R^2$ is selected from the group consisting of hydrogen; $C_{1-4}$alkyleneheteroaryl, wherein the heteroaryl group is selected from the group consisting of benzimidazole, a triazole, and imidazole; $C_{1-4}$alkyleneHet, wherein Het is selected from the group consisting of piperazine, morpholine, pyrrolidine, pyrrolidone, tetrahydrofuran, piperidine,

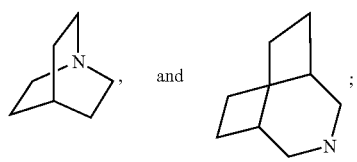

$C_{1-4}$alkyleneC$_6$H$_5$, optionally substituted with one to three groups selected from the group consisting of C(=O)$OR^a$, $NR^aR^b$, $NR^aSO_2CF_3$, $SO_2NR^aR^b$, CN, $OR^a$, C(=O)$R^a$, $C_{1-4}$alkyleneNR$^aR^b$, nitro, OC$_{1-4}$alkylenearyl, and OC$_{1-4}$alkyleneNRaRb; $C_{1-4}$alkyleneC(=O)benzyl; $C_{1-4}$alkyleneC(=O)$OR^a$; $C_{1-4}$alkyleneC(=O)$NR^aR^b$; $C_{1-4}$alkyleneC(=O)$NR^aR^c$; $C_{1-4}$alkyleneHet; $NR^aR^b$; OH; OC$_{1-4}$alkyl; C$_6$H$_5$; $C_{1-4}$alkyleneNR$^aR^b$; $C_{1-4}$alkyleneOR$^a$; $C_{1-4}$alkyleneNHC(=O)$R^a$; and $C_{1-4}$alkyleneOC$_{1-4}$alkyleneOR$^a$.

30. The compound of claim 21 wherein $R^2$ is selected from the group consisting of $C_{1-6}$alkyl, C(=O)$OR^a$, C(=O)$R^a$, hydrogen, C(=O)$NR^aC_{1-4}$alkyleneHet, C(=O)$NR^aR^c$, aryl, and heteroaryl.

31. The compound of claim 21 wherein $R^3$ is selected from the group consisting of C(=O)$R^b$, C(=O)$NR^aC_{1-4}$alkyleneOC$_{1-6}$alkyl, C(=O)$NR^aC_{1-4}$alkyleneC$_{3-8}$cycloalkyl, C(=O)Het,

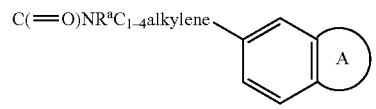

C(=O)$NR^aC_{1-4}$alkyleneheteroaryl, C(=O)$NR^aC_{1-4}$alkylenearyl, C(=O)$NR^aC_{1-4}$alkyleneHet, C(=O)$NR^aR^c$, and C(=S)$NR^aR^c$.

32. The compound of claim 21 wherein $R^4$ selected from the group consisting of hydrogen, $C_{1-6}$alkyl, aryl, and heteroaryl.

33. The compound of claim 21 wherein q is 0, or $R^0$ is selected from the group consisting of halo, methyl, trifluoromethyl, and trifluoromethyl; $R^1$ is selected from the group consisting of

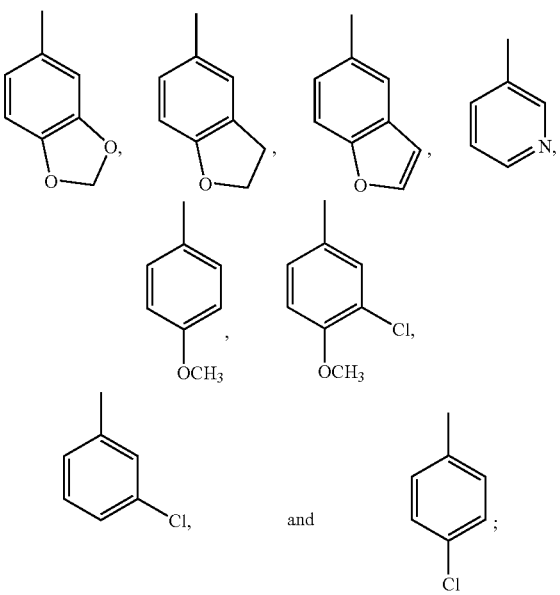

$R^2$ is selected from the group consisting of hydrogen, $C_{1-6}$alkyl, C(=O)$NR^aR^c$, and $C_{1-4}$alyleneHet; $R^3$ is selected from the group consisting of C(=O)NHCH$_2$C$_6$H$_5$, C(=O)NH(CH$_2$)$_2$C$_6$H$_5$, C(=O)NHC$_6$H$_5$, C(=O)NH$_2$, C(=O)N(CH$_3$)$_2$, C(=S)N(CH$_3$)$_2$, C(=O)NH(CH$_2$)$_2$CH$_3$, C(=O)N(CH$_2$)$_3$CH$_3$, C(=O)NHCH$_3$, C(=O)NHCH(CH$_3$)$_2$, C(=O)NH(CH$_2$)$_3$OCH$_3$,

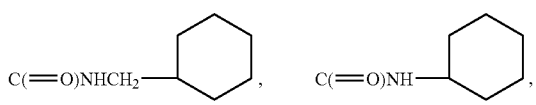

-continued
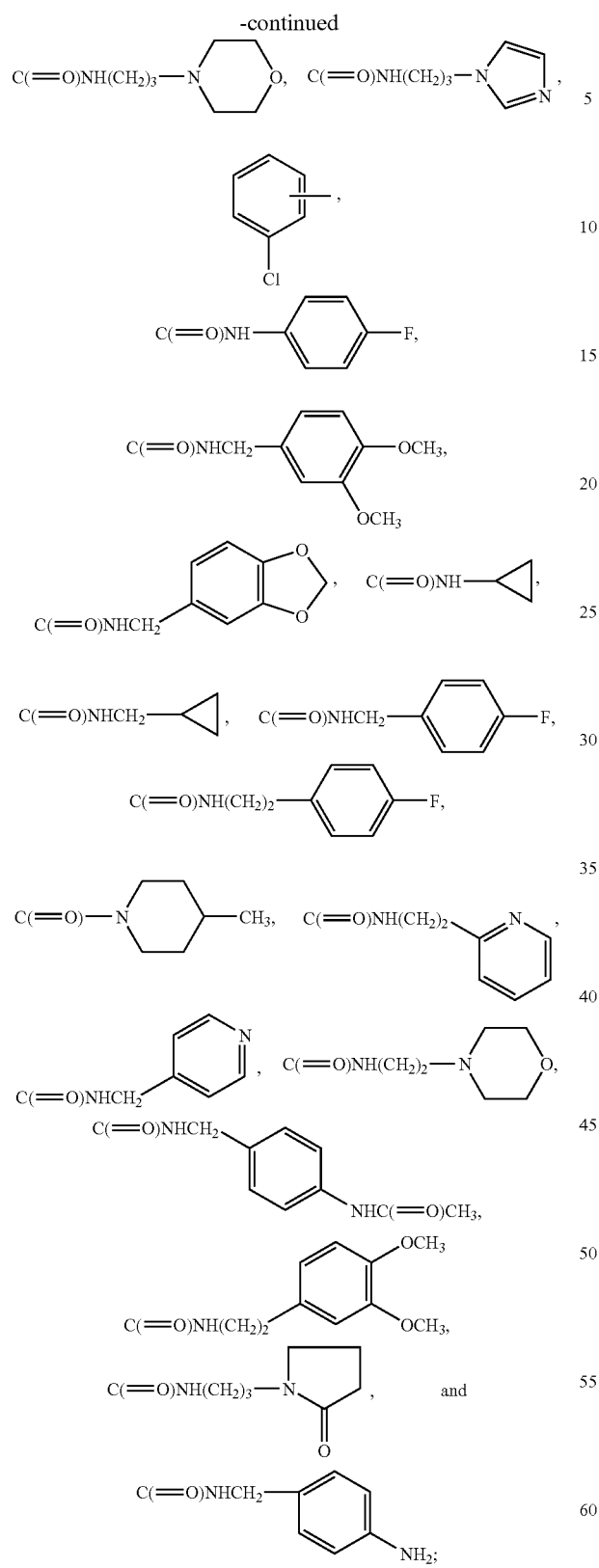
and R[4] is hydrogen and $C_{1-6}$alkyl.
34. The compound of claim 21 wherein q is 0, R[2] is hydrogen, and R[4] is hydrogen or methyl.
35. A compound selected from the group consisting of
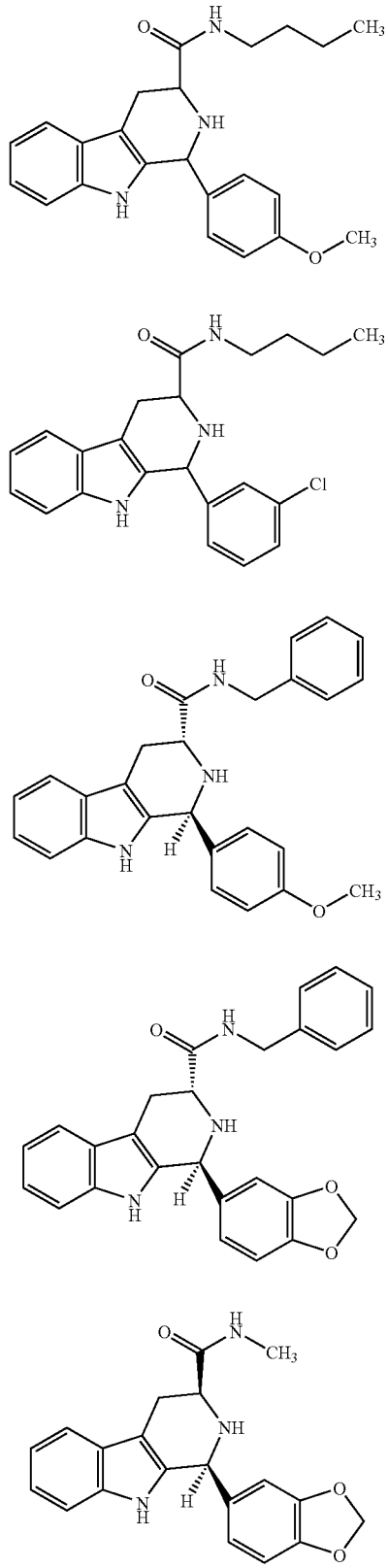

-continued
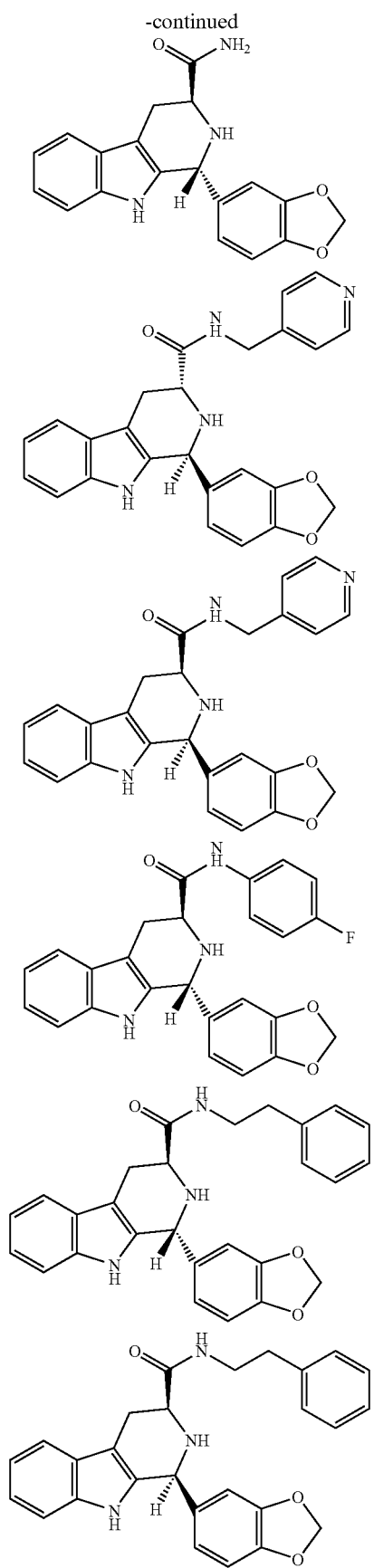
-continued
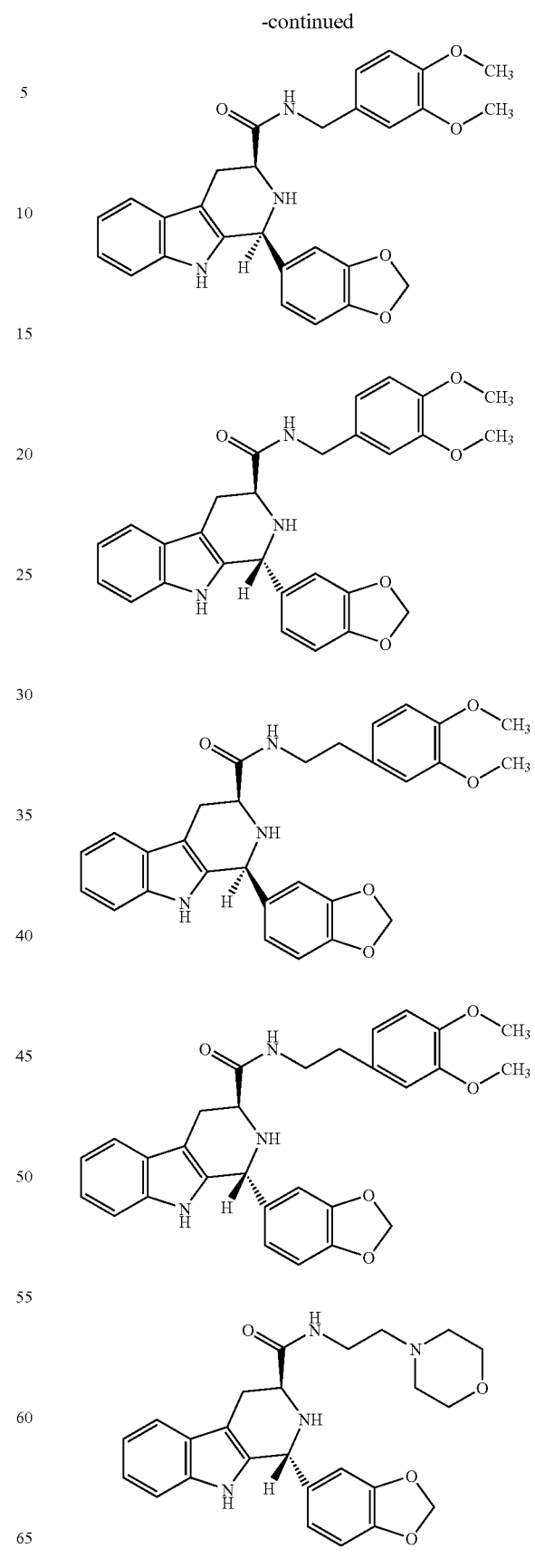

-continued
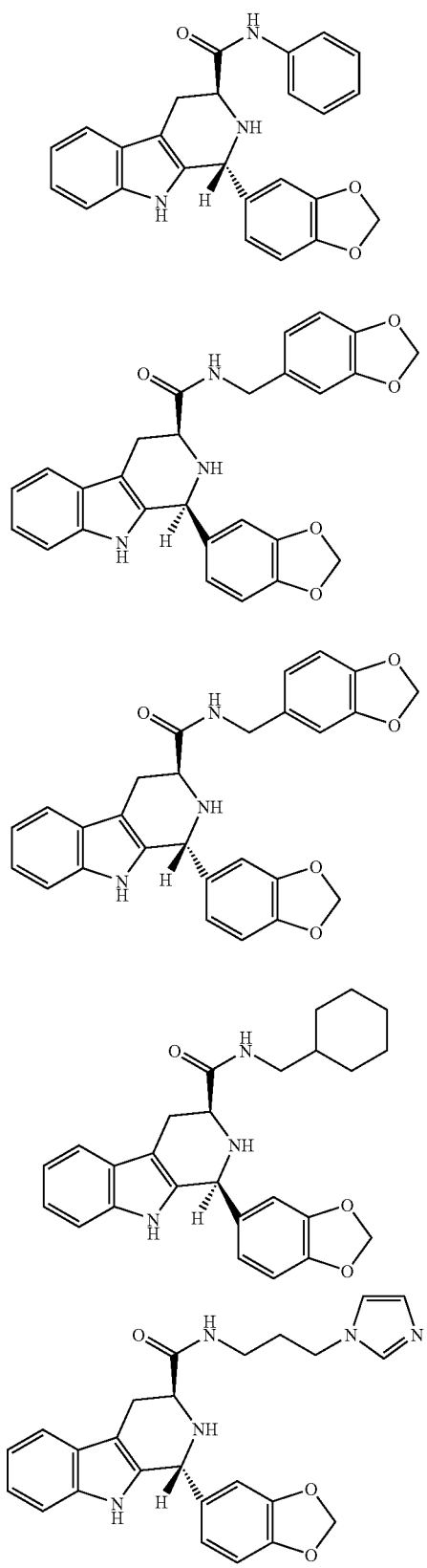
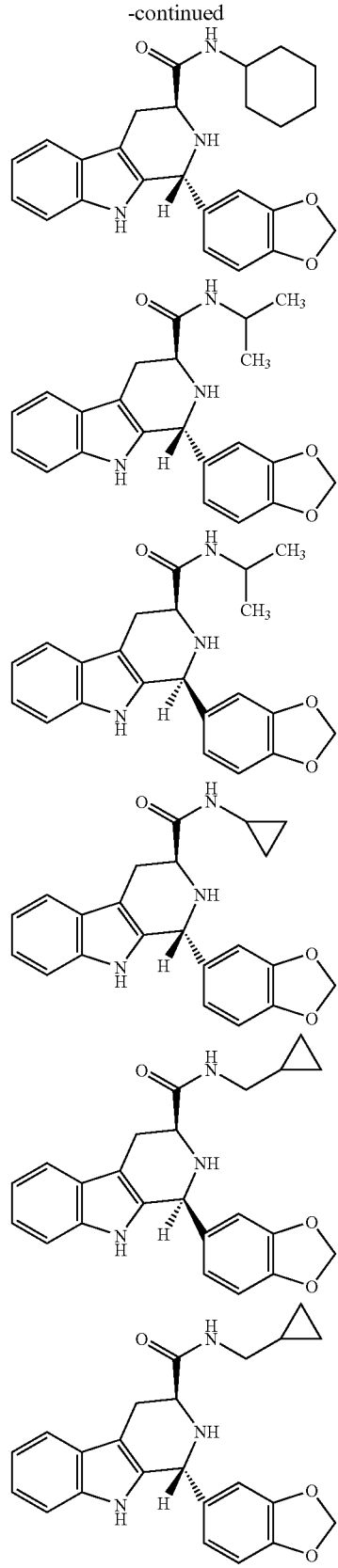

-continued
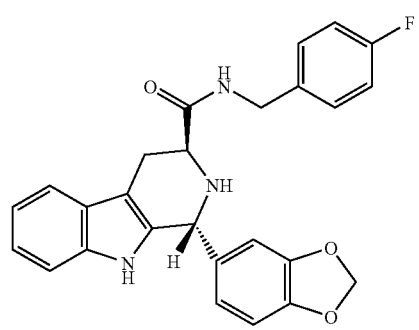
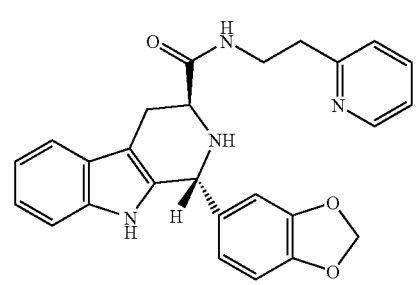
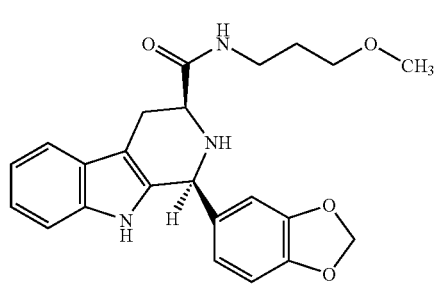
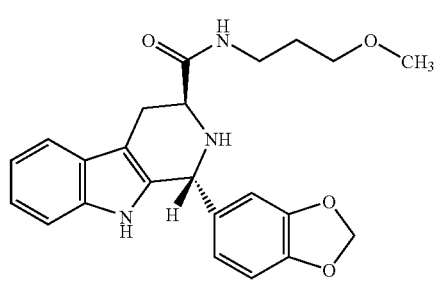
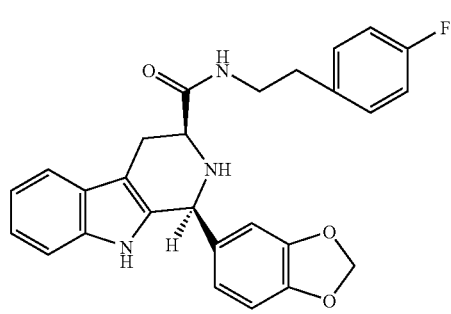
-continued
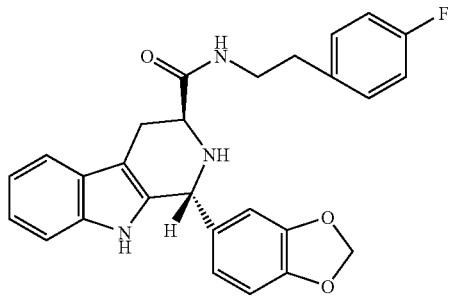
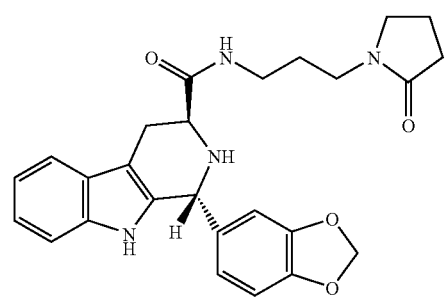
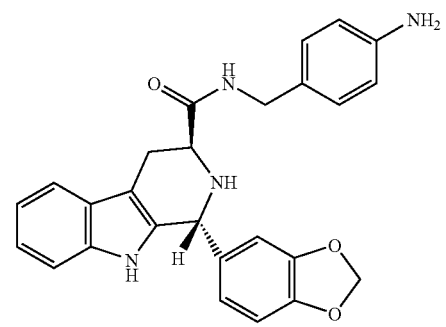
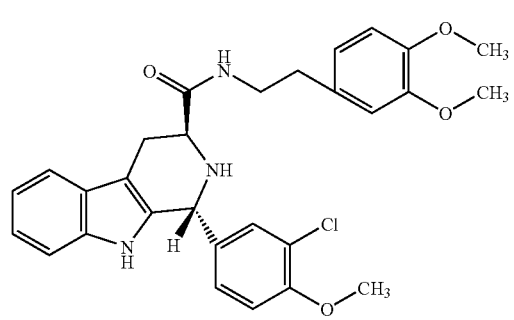
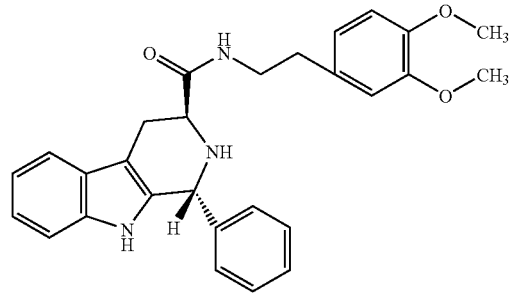

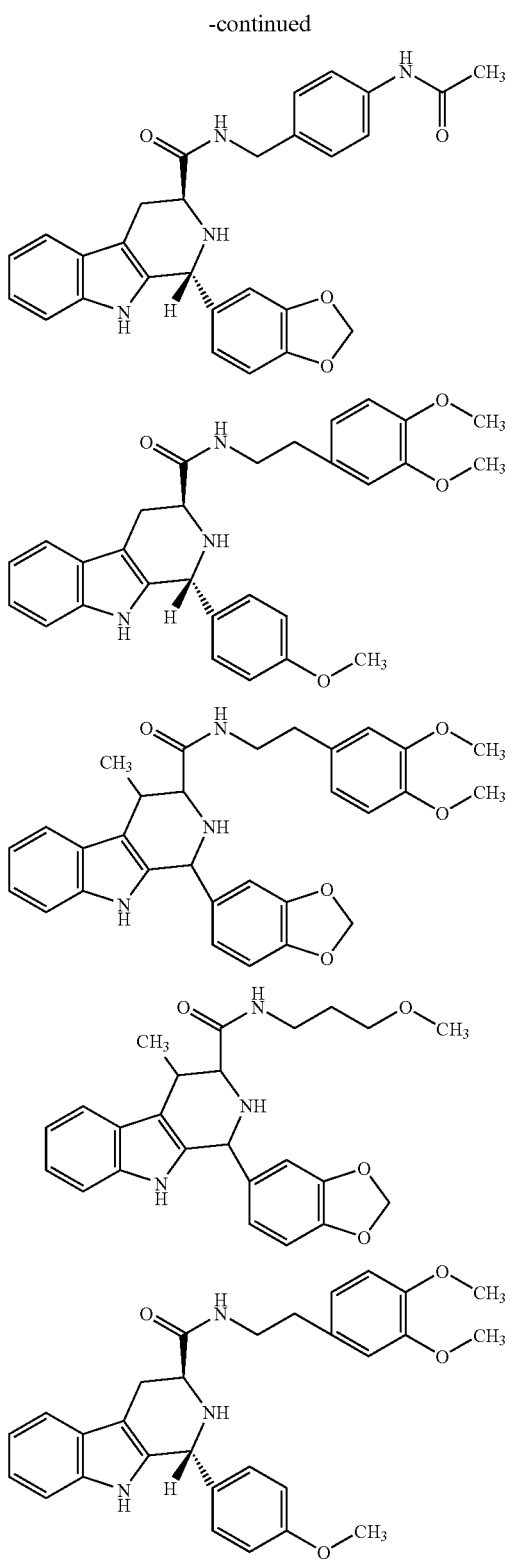
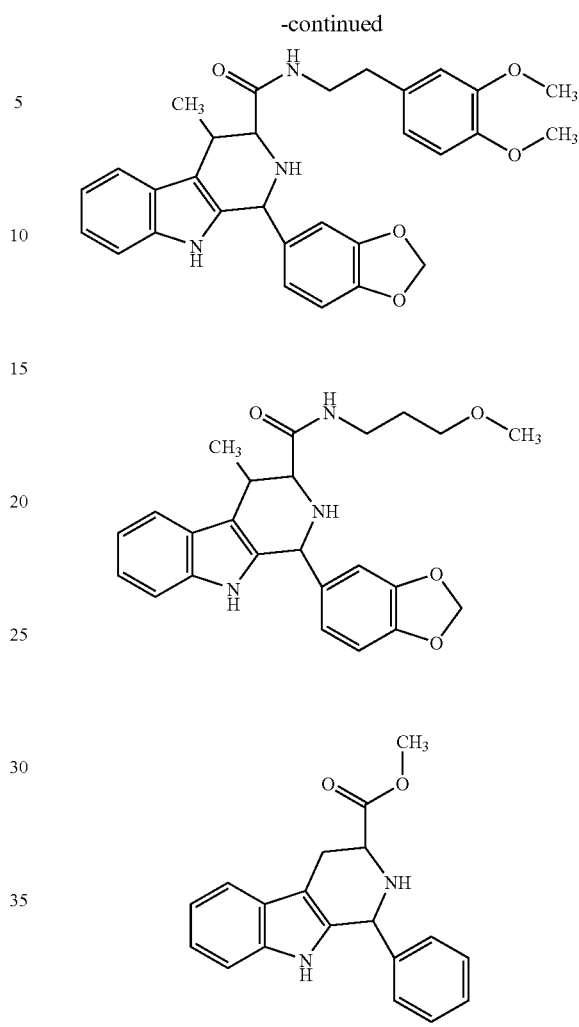

or a pharmaceutically acceptable salt or solvate thereof.

36. A pharmaceutical composition comprising a compound of claim 21, together with a pharmaceutically acceptable diluent or carrier.

37. A method of treating a male animal for male erectile dysfunction comprising administering to said male animal an effective amount of a pharmaceutical composition comprising a compound of claim 21, together with a pharmaceutically acceptable diluent or carrier.

38. The method of claim 37 wherein the treatment is an oral treatment.

39. A method for prophylactic treatment of male erectile dysfunction comprising administration of an effective dose of a compound of claim 21, or a pharmaceutically acceptable salt or solvate thereof, to a male animal.

* * * * *